(12) United States Patent
Boyd et al.

(10) Patent No.: US 6,552,036 B2
(45) Date of Patent: Apr. 22, 2003

(54) 3-(DIARYLMETHYLENE)-8-AZABICYCLO[3.2.1]OCTANE DERIVATIVES

(75) Inventors: Robert E. Boyd, Horsham, PA (US); John R. Carson, Norristown, PA (US); Steven J. Coats, Quakertown, PA (US); Lou Anne Neilson, Sellersville, PA (US); Philip M Pitis, North Wales, PA (US); Wu-Nan Wu, Landsdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/791,246

(22) Filed: Feb. 22, 2001

(65) Prior Publication Data

US 2002/0115662 A1 Aug. 22, 2002

Related U.S. Application Data

(60) Provisional application No. 60/186,778, filed on Mar. 3, 2000.

(51) Int. Cl.[7] ............... C07D 451/02; A61K 31/44
(52) U.S. Cl. ......................... 514/299; 546/112
(58) Field of Search ................ 546/112; 514/299

(56) References Cited

FOREIGN PATENT DOCUMENTS

| WO | WO 93/15062 A1 | 8/1993 |
|---|---|---|
| WO | WO 97/23466 A1 | 7/1997 |
| WO | WO 98/28270 A1 | 7/1998 |
| WO | WO 98/28275 A1 | 7/1998 |

OTHER PUBLICATIONS

Paten Abstracts of Japan vol. 018, No. 443 (c–1239), Aug. 18, 1994—& JP 06 135965 A (Toray Ind Inc), May 17, 1994 abstract.

Thomas, J.B., Atkinson, R.N., Rothman, R.B., Burgess, J.P., Mascarella, S.W., Dersch, C.M., XU, H. and Carroll, F.I., Biorg. Med. Chem. Lett., 2000, 10:1281–1284.

Boyd, R.E., Carson, J.R., Codd, E.E., Gauthier, A.D., Neilson, L.A. and Zhang, S–P.,, Biorg. Med Chem. Lett., 2000, 10: 1109–1111.

Gutkowska, B., et al., Acta Pol. Pharm., 1984, 41(6), 613–617.

*Primary Examiner*—Bruce Kifle

(57) ABSTRACT

This invention is directed to 3-(diarylmethylene)-8-azabicyclo[3.2.1]octane derivatives useful as δ-opioid or μ-opioid receptor modulators. Depending on their agonist or antagonist effect, the compounds are useful analgesics, immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases.

25 Claims, No Drawings

3-(DIARYLMETHYLENE)-8-AZABICYCLO[3.2.1]OCTANE DERIVATIVES

This application claims the benefit of U.S. Provisional Application No. 60/186,778 filed Mar., 3, 2000.

FIELD OF THE INVENTION

The present invention is directed to compounds useful as delta-opioid and mu-opioid receptor modulators. More particularly, the present invention is directed to 3-(diarylmethylene)-8-azabicyclo[3.2.1]octane derivatives useful as delta-opioid or mu-opioid receptor modulators.

BACKGROUND OF THE INVENTION

WO 97/23466 describes compounds as having an analgesic effect of a general and one preferred formula:

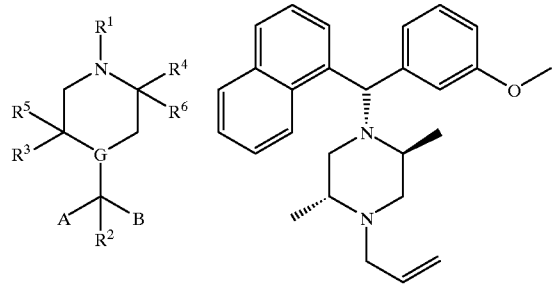

WO 98/28270 describes compounds as having an analgesic effect of a general and one preferred formula:

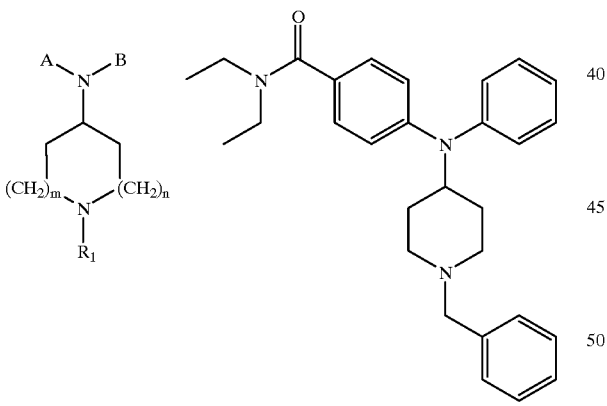

WO 98/28275 describes compounds as having an analgesic effect of a general and one preferred formula:

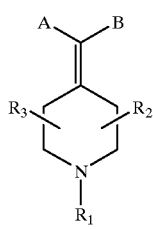

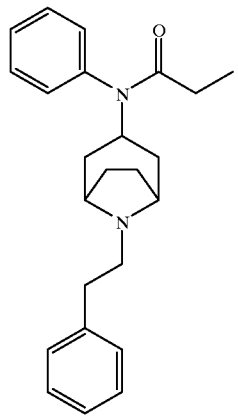

Amide derivatives of 3-aminotropane have been prepared and described as having potential pharmacological activity (Gutkowska, B., et al., *Acta Pol. Pharm.*, 1984, 41(6), 613–617), of the formula:

WO 93/15062 describes compounds as delta-opioid (δ-opioid) and mu-opioid (μ-opioid) receptor agonists of (approximately) the general formula:

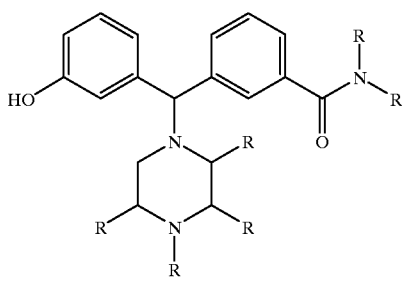

The synthesis and binding affinities for 4-Diarylaminotropane compounds as δ-opioid agonists have been described (Boyd, R. E., Carson, J. R., Codd, E. E., Gauthier, A. D., Neilson, L. A and Zhang, S-P., *Biorg. Med. Chem. Lett.*, 2000, 10: 1109–1111) of the general formula:

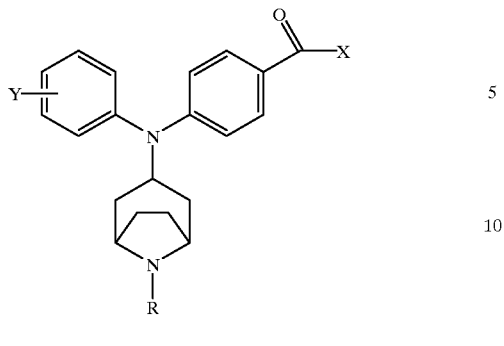

wherein R is hydrogen, methyl, propyl, hexyl, 2-ethylbutyl, allyl, 3,3-dimethallyl, cyclohexylmethyl, phenethyl, phenylpropyl, 2,2-diphenylethyl, 3,4-dimethoxyphenethyl, 4-fluorophenethyl, 2-furylmethyl, 3,4-methylenedioxybenzyl, cyano and X is N,N-dimethylamino, N,N-diethylamino, N,N-dipropylamino, N-methyl-N-ethylamino, N-methyl-N-propylamino, N-methyl-N-phenylamino, N-ethyl-N-(4-methyl)benzylamino, N-butyl-N-ethylamino, N-butyl-N-propylamino, [N-ethyl-N-(2-methyl)allyl]amino, hydroxy, O-t-butyl and 1-pyrrolidinyl; and, Y is hydrogen, methoxy and methylthio.

Other selective 4-[(8-alkyl-8-azabicyclo[3.2.1] octyl-3-yl)-3-arylanilino]-N,N-diethylbenzamide δ-opioid ligands have also been described (Thomas, J. B., Atkinson, R. N., Rothman, R. B., Burgess, J. P., Mascarella, S. W., Dersch, C. M., Xu, H. and Carroll, F. I., *Biorg. Med. Chem. Lett.,* 2000, 10: 1281–1284).

The present invention is directed to compounds useful as delta-opioid and mu-opioid receptor modulators. More particularly, the present invention is directed to delta-opioid and mu-opioid receptor modulators.

It is an object of the present invention to provide 3-(diarylmethylene)-8-azabicyclo[3.2.1]octane derivatives useful as δ-opioid or μ-opioid receptor modulators. It is also an object of the present invention to provide δ-opioid and μ-opioid receptor selective agonists as analgesics having reduced side-effects. It is another object of the present invention to provide δ-opioid and μ-opioid receptor selective antagonists as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects. It is also another object of the present invention to provide a useful pharmaceutical composition comprising a compound of the present invention useful as a δ-opioid or μ-opioid receptor modulator. It is a further object of the present invention to provide a useful pharmaceutical composition comprising a δ-opioid or μ-opioid receptor modulator compound of Formula (I) in combination with a μ-opioid receptor modulator or a δ-opioid or μ-opioid receptor modulator compound of Formula (I) wherein the combination has a synergistic therapeutic effect.

SUMMARY OF THE INVENTION

The present invention provides an opioid receptor modulator compound selected from the group consisting of a δ-opioid and a μ-opioid receptor modulator compound of Formula (I):

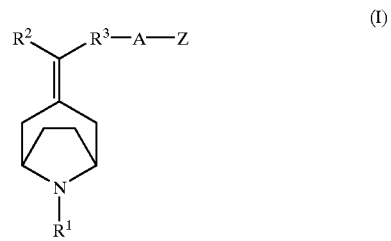

wherein:

$R^1$ is selected from the group consisting of hydrogen, $C_{1-8}$alkyl, $halo_{1-3}(C_{1-8})$alkyl, $C_{2-8}$alkenyl, $C_{1-8}$alkoxy $(C_{2-8})$alkenyl, $C_{2-8}$alkynyl, $C_{1-8}$alkoxy$(C_{2-8})$alkynyl, cycloalkyl, cycloalkyl$(C_{1-8})$alkyl, cycloalkylcarbonyl $(C_{1-8})$alkyl, cycloalkyl$(C_{2-8})$alkenyl, cycloalkyl$(C_{2-8})$alkynyl, heterocyclyl, heterocyclyl$(C_{1-8})$alkyl, heterocyclylcarbonyl $(C_{1-8})$alkyl, heterocyclyl$(C_{2-8})$alkenyl, heterocyclyl$(C_{2-8})$alkynyl, aryl, aryl$(C_{1-8})$alkyl, arylcarbonyl$(C_{1-8})$alkyl, aryl$(C_{2-8})$alkenyl, aryl$(C_{2-8})$alkynyl, arylaminocarbonyl$(C_{1-8})$alkyl, heteroaryl $(C_{1-8})$alkyl, heteroarylcarbonyl$(C_{1-8})$alkyl, heteroaryl $(C_{2-8})$alkenyl, heteroaryl$(C_{2-8})$alkynyl, heteroarylaminocarbonyl$(C_{1-8})$alkyl, $(R^{1a})_2$—N—$(C_{1-8})$alkyl, $R^{1a}$—O—$(C_{1-8})$alkyl, $R^{1a}$—S—$(C_{1-8})$alkyl, $R^{1a}$—SO—$(C_{1-8})$alkyl and $R^{1a}$—SO$_2$—$(C_{1-8})$alkyl; wherein heterocyclyl is optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, oxo, cyano, trifluoromethyl and trifluoromethoxy; and, wherein aryl and heteroaryl are optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy;

$R^{1a}$ is independently selected from the group consisting of hydrogen, $C_{1-8}$alkyl, $C_{1-8}$alkoxy$(C_{1-8})$alkyl, hydroxy $(C_{1-8})$alkyl, $halo_{1-3}(C_{1-8})$alkyl, $halo_{1-3}(C_{1-8})$alkoxy $(C_{1-8})$alkyl, $C_{2-8}$alkenyl, $C_{2-8}$alkynyl, cycloalkyl, cycloalkyl$(C_{1-8})$alkyl, heterocyclyl, heterocyclyl$(C_{1-8})$alkyl, heterocyclyl$(C_{1-8})$alkenyl, heterocyclyl$(C_{1-8})$alkynyl, aryl, aryl$(C_{1-8})$alkyl, aryl$(C_{1-8})$alkenyl, aryl $(C_{1-8})$alkynyl, arylcarbonyl$(C_{1-8})$alkyl, heteroaryl, heteroaryl$(C_{1-8})$alkyl, heteroaryl$(C_{1-8})$alkenyl, heteroaryl$(C_{1-8})$alkynyl and heteroarylcarbonyl$(C_{1-8})$ alkyl; wherein heterocyclyl is optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, oxo, cyano, trifluoromethyl and trifluoromethoxy; and, wherein aryl and heteroaryl are optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy;

$R^2$ is selected from the group consisting of aryl and heteroaryl optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkyloxycarbonyl, $C_{1-6}$alkylaminocarbonyl, $C_{1-6}$alkylcarbonylamino, $C_{1-6}$alkylthio, $C_{1-6}$alkylsulfonyl, halogen, hydroxy, cyano, trifluoromethyl and trifluoromethoxy; alternatively, when aryl and heteroaryl are substituted with two substituents attached to adjacent carbon atoms, the two substituents can together form a single fused moiety; wherein the moiety is selected from the group consisting of —($CH_2$)$_{3-5}$— and —O($CH_2$)$_{1-3}$O—;

$R^3$ is selected from the group consisting of aryl and heteroaryl optionally substituted with one or two substituents in addition to the -A-Z moiety independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkyloxycarbonyl, $C_{1-6}$alkylaminocarbonyl, $C_{1-6}$alkylcarbonylamino, $C_{1-6}$alkylthio, $C_{1-6}$alkylsulfonyl, halogen, hydroxy, cyano, trifluoromethyl and trifluoromethoxy; alternatively, when aryl and heteroaryl are substituted with two optional substituents attached to adjacent carbon atoms, the two substituents can together form a single fused moiety; wherein the moiety is selected from the group consisting of —($CH_2$)$_{3-5}$— and —O($CH_2$)$_{1-3}$O—;

A is selected from the group consisting of —C(=X)— and —$SO_2$—;

X is selected from the group consisting of O and S;

Z is selected from the group consisting of —O($R^4$) and —N($R^5$)($R^6$);

$R^4$ is selected from the group consisting of hydrogen, $C_{1-8}$alkyl (optionally substituted with one to three halogen substituents), $C_{1-8}$alkoxy($C_{1-8}$)alkyl, $C_{2-8}$alkenyl, cycloalkyl, cycloalkyl($C_{1-8}$)alkyl, heterocyclyl, heterocyclyl($C_{1-8}$)alkyl, aryl, aryl($C_{1-8}$)alkyl, heteroaryl, heteroaryl($C_{1-8}$)alkyl, amino($C_{1-8}$)alkyl, $C_{1-8}$alkylamino($C_{1-8}$)alkyl, di($C_{1-8}$)alkylamino($C_{1-8}$)alkyl and hydroxy($C_{1-8}$)alkyl; wherein heterocyclyl is optionally substituted with one to three substituents independently selected from the group consisting of $C_{1-6}$alkyl, $C_{1-6}$alkoxy, $C_{2-6}$alkenyl, cycloalkyl, trifluoromethyl, halogen, hydroxy, oxo and cyano; and, wherein aryl is optionally substituted with one to four substituents independently selected from the group consisting of $C_{1-6}$alkyl, $C_{1-6}$alkoxy, $C_{2-6}$alkenyl, cycloalkyl, —OCH$_2$O—, —O(CH$_2$)$_2$O—, trifluoromethyl, halogen, hydroxy and cyano; and, $R^5$ and $R^6$ are independently selected from the group consisting of hydrogen, $C_{1-8}$alkyl (optionally substituted with one to three halogen substituents), $C_{1-8}$alkoxy($C_{1-8}$)alkyl, $C_{2-8}$alkenyl, cycloalkyl, cycloalkyl($C_{1-8}$)alkyl, heterocyclyl, heterocyclyl($C_{1-8}$)alkyl, aryl, aryl($C_{1-8}$)alkyl, heteroaryl, heteroaryl($C_{1-8}$)alkyl, amino($C_{1-8}$)alkyl, $C_{1-8}$alkylamino($C_{1-8}$)alkyl, di($C_{1-8}$)alkylamino($C_{1-8}$)alkyl, aminoimino, aminocarbonyl, aminocarbonyl($C_{1-8}$)alkyl, aryloxycarbonylamino($C_{1-8}$)alkyl, heteroaryloxycarbonylamino($C_{1-8}$)alkyl, hydroxy($C_{1-8}$)alkyl and trifluoro($C_{1-4}$)alkoxy; wherein heterocyclyl is optionally substituted with one to three substituents independently selected from the group consisting of $C_{1-6}$alkyl, $C_{1-6}$alkoxy, $C_{2-6}$alkenyl, cycloalkyl, trifluoromethyl, halogen, hydroxy, oxo and cyano; and, wherein aryl is optionally substituted with one to four substituents independently selected from the group consisting of $C_{1-6}$alkyl, $C_{1-6}$alkoxy, $C_{2-6}$alkenyl, cycloalkyl, —OCH$_2$O—, —O(CH$_2$)$_2$O—, trifluoromethyl, halogen, hydroxy and cyano; alternatively, $R^5$ and $R^6$ may, together with the nitrogen to which they are attached, form a fused heterocyclyl moiety optionally substituted with one to four substituents independently selected from the group consisting of $C_{1-6}$alkyl, $C_{1-6}$alkoxy, $C_{2-6}$alkenyl, cycloalkyl, trifluoromethyl, halogen, hydroxy and cyano;

and pharmaceutically acceptable enantiomers, diastereomers and salts thereof.

DETAILED DESCRIPTION OF THE INVENTION

Embodiments of a compound of Formula (I) include those compounds wherein, preferably, $R^1$ is selected from the group consisting of hydrogen, $C_{1-8}$alkyl, $C_{2-8}$alkenyl, $C_{2-8}$alkynyl, cycloalkyl, cycloalkyl($C_{1-8}$)alkyl, heterocyclyl, heterocyclyl($C_{1-8}$)alkyl, heterocyclylcarbonyl($C_{1-8}$)alkyl, aryl($C_{1-8}$)alkyl, arylcarbonyl($C_{1-8}$)alkyl, aryl($C_{2-8}$)alkynyl, arylaminocarbonyl($C_{1-8}$)alkyl, heteroaryl($C_{1-8}$)alkyl, ($R^{1a}$)$_2$—N—($C_{1-8}$)alkyl and $R^{1a}$—O—($C_{1-8}$)alkyl; wherein heterocyclyl is optionally substituted with one to three substituents independently selected from the group consisting of $C_{1-6}$alkyl, $C_{1-6}$alkoxy, halogen, hydroxy, oxo and cyano; and, wherein aryl is optionally substituted with one to three substituents independently selected from the group consisting of $C_{1-6}$alkyl, $C_{1-6}$alkoxy, halogen, hydroxy and cyano.

More preferably, $R^1$ is selected from the group consisting of hydrogen, methyl, ethyl, n-propyl, i-propyl, n-butyl, t-butyl, n-hexyl, butenyl, allyl, 3,3-dimethallyl, cyclopropyl, cyclopropyl($C_{1-3}$)alkyl, cyclohexyl, cyclohexyl($C_{1-3}$)alkyl, pyrrolidinyl, pyrrolidinyl($C_{1-3}$)alkyl, 1,3-dioxolanyl($C_{1-3}$) alkyl, 2-imidazolinyl, 2-imidazolinyl($C_{1-3}$)alkyl, imidazolidinyl, imidazolidinyl($C_{1-3}$)alkyl, 2-pyrazolinyl, 2-pyrazolinyl($C_{1-3}$)alkyl, pyrazolidinyl, pyrazolidinyl($C_{1-3}$) alkyl, piperidinyl, piperidinyl($C_{1-3}$)alkyl, morpholinyl, morpholinyl($C_{1-3}$)alkyl, thiomorpholinyl, thiomorpholinyl ($C_{1-3}$)alkyl, piperazinyl, piperazinyl($C_{1-3}$)alkyl, [4-($C_{1-3}$) alkyl-5-oxo-1,4-dihydrotetrazol-1-yl]($C_{1-3}$)alkyl, piperonyl, (1,3-benzodioxol-5-yl)($C_{2-3}$)alkyl, (2,3-dihydro-1,4-benzodioxin-6-yl)carbonyl($C_{1-3}$)alkyl, (3,4-dihydro-2H-1, 5-benzodioxepin-7-yl)carbonyl($C_{1-3}$)alkyl, benzyl, phenyl ($C_{2-3}$)alkyl, phenyl($C_{2-3}$)alkynyl, diphenyl($C_{1-3}$)alkyl, phenylcarbonyl($C_{1-3}$)alkyl, phenylaminocarbonyl($C_{1-3}$) alkyl, furyl($C_{1-3}$)alkyl, thienyl($C_{1-3}$)alkyl, pyrrolyl($C_{1-3}$) alkyl, oxazolyl($C_{1-3}$)alkyl, thiazolyl($C_{1-3}$)alkyl, imidazolyl ($C_{1-3}$)alkyl, pyrazolyl($C_{1-3}$)alkyl, isoxazolyl($C_{1-3}$)alkyl, isothiazolyl($C_{1-3}$)alkyl, 1,2,3-oxadiazolyl($C_{1-3}$)alkyl, 1,2,3-triazolyl($C_{1-3}$)alkyl, 1,3,4-thiadiazolyl($C_{1-3}$)alkyl, pyridinyl ($C_{1-3}$)alkyl, pyridazinyl($C_{1-3}$)alkyl, pyrimidinyl($C_{1-3}$)alkyl, pyrazinyl($C_{1-3}$)alkyl, 1,3,5-triazinyl($C_{1-3}$)alkyl, indolyl ($C_{1-3}$)alkyl, benzo[b]furyl($C_{1-3}$)alkyl, benzo[b]thienyl($C_{1-3}$) alkyl, ($R^{1a}$)$_2$—N—($C_{1-3}$)alkyl and $R^{1a}$—O—($C_{1-3}$)alkyl; wherein pyrrolidinyl, 2-imidazolinyl, imidazolidinyl, 2-pyrazolinyl, pyrazolidinyl, piperidinyl, morpholinyl, thiomorpholinyl and piperazinyl are optionally substituted with one to three substituents selected from oxo; and, wherein phenyl is optionally substituted with one to three substituents independently selected from the group consisting of methyl, ethyl, n-propyl, n-butyl, methoxy, ethoxy, propoxy, butoxy, chlorine, fluorine, hydroxy and cyano.

Most preferably, $R^1$ is selected from the group consisting of hydrogen, methyl, n-propyl, n-butyl, allyl, 3,3-dimethallyl, cyclopropylmethyl, cyclohexylethyl, 2-(4-ethyl-5-oxo-1,4-dihydrotetrazol-1-yl)ethyl, piperonyl, 2-(1,3-benzodioxol-5-yl)ethyl, 2-(2,3-dihydro-1,4-benzodioxin-6-yl)-2-oxoethyl, 2-(3,4-dihydro-2H-1,5-benzodioxepin-7-yl)-2-oxoethyl, benzyl, phenethyl, phenylpropyl, phenoxyethyl, phenylcarbonylmethyl, phenylcarbonylethyl, phenylaminocarbonylmethyl, thienylmethyl, thienylethyl, imidazolylmethyl, pyridinylmethyl and indolylethyl; wherein phenyl is optionally substituted with one to three substituents independently selected from the group consisting of methoxy, fluorine, hydroxy and cyano.

Embodiments of a compound of Formula (I) include those compounds wherein, preferably, $R^{1a}$ is independently selected from the group consisting of hydrogen, $C_{1-8}$alkyl and aryl; wherein aryl is optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy. More preferably, $R^{1a}$ is independently selected from the group consisting of hydrogen, methyl, ethyl, n-propyl, i-propyl, n-butyl, t-butyl and phenyl; wherein phenyl is optionally substituted with one to three substituents independently selected from the group consisting of $C_{1-6}$alkyl, $C_{1-6}$alkoxy, di($C_{1-6}$alkyl) amino, halogen, trifluoromethyl and trifluoromethoxy. Most preferably, $R^{1a}$ is independently selected from the group consisting of methyl, ethyl and phenyl.

Embodiments of a compound of Formula (I) include those compounds wherein, preferably, $R^2$ is selected from the group consisting of phenyl, naphthalenyl, furyl, thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridinyl, pyridazinyl, pyrimidinyl, pyrazinyl, 1,3,5-triazinyl, indolyl, benzo[b]furyl and benzo[b]thienyl optionally substituted with one to three substituents independently selected from the group consisting of $C_{1-3}$alkyl, $C_{2-3}$alkenyl, $C_{1-3}$alkoxy, amino, $C_{1-3}$alkylamino, di($C_{1-3}$alkyl)amino, $C_{1-3}$alkylcarbonyl, $C_{1-3}$alkylcarbonyloxy, $C_{1-3}$alkylcarbonylamino, chlorine, fluorine, hydroxy, trifluoromethyl and trifluoromethoxy.

More preferably, $R^2$ is selected from the group consisting of phenyl, furyl, thienyl, pyridinyl and benzo[b]furyl optionally substituted with one substituent selected from the group consisting of methyl, ethyl, methoxy, ethoxy, methylamino, ethylamino, dimethylamino, diethylamino, methylcarbonyl, methylcarbonyloxy, methylcarbonylamino, fluorine, hydroxy, trifluoromethyl and trifluoromethoxy.

Most preferably, $R^2$ is selected from phenyl optionally substituted with one substituent selected from the group consisting of methoxy and hydroxy.

Embodiments of a compound of Formula (I) include those compounds wherein, preferably, $R^3$ is selected from the group consisting of phenyl, naphthalenyl, furyl, thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridinyl, pyridazinyl, pyrimidinyl, pyrazinyl, 1,3,5-triazinyl, indolyl, benzo[b]furyl and benzo[b]thienyl optionally substituted with one or two substituents in addition to the -A-Z moiety independently selected from the group consisting of methyl, ethyl, n-propyl, i-propyl, allyl, methoxy, ethoxy, amino, $C_{1-3}$alkylamino, di($C_{1-3}$)alkylamino, $C_{1-3}$alkylcarbonyl, $C_{1-3}$alkylcarbonyloxy, $C_{1-3}$alkylcarbonyl, $C_{1-3}$alkylaminocarbonyl, $C_{1-3}$alkylcarbonylamino, $C_{1-3}$alkylthio, $C_{1-3}$alkylsulfonyl, chloro, fluoro, hydroxy, cyano, trifluoromethyl and trifluoromethoxy; alternatively, when phenyl is substituted with two optional substituents attached to adjacent carbon atoms, the two substituents can together form a single fused moiety; wherein the moiety is selected from the group consisting of —(CH$_2$)$_{3-5}$— and —O(CH$_2$)$_{1-3}$O—.

More preferably, $R^3$ is phenyl substituted with the moiety -A-Z at the 3 or 4 position.

Embodiments of a compound of Formula (I) include those compounds wherein, preferably, A is —C(=X)—.

Embodiments of a compound of Formula (I) include those compounds wherein, preferably, Z is —N($R^5$)($R^6$).

An embodiment of a compound of Formula (I) includes those compounds wherein, preferably, $R^4$ is selected from the group consisting of $C_{1-8}$alkyl (optionally substituted with one to three halogen substituents), $C_{2-8}$alkenyl, aryl and aryl($C_{1-8}$)alkyl; wherein aryl is optionally substituted with one to two substituents independently selected from the group consisting of $C_{1-8}$alkyl, —OCH$_2$O—, —O(CH$_2$)$_2$O— and halogen.

More preferably, $R^4$ is selected from the group consisting of $C_{1-3}$alkyl (optionally substituted with one or three fluorine substituents), $C_{2-4}$alkenyl, phenyl and benzyl; wherein phenyl is optionally substituted with one to two substituents independently selected from the group consisting of $C_{1-3}$alkyl, —OCH$_2$O—, —O(CH$_2$)$_2$O— and fluorine.

Most preferably, $R^4$ is selected from the group consisting of methyl, ethyl, 3-methallyl, phenyl and benzyl; wherein phenyl is optionally substituted with one substituent selected from the group consisting of methyl and fluorine.

An embodiment of a compound of Formula (I) includes those compounds wherein, preferably, $R^5$ and $R^6$ are independently selected from the group consisting of hydrogen, $C_{1-4}$alkyl, fluoro($C_{1-3}$)alkyl, trifluoro($C_{1-3}$)alkyl, $C_{1-3}$alkoxy ($C_{1-3}$)alkyl, $C_{2-5}$alkenyl, cyclopropyl, cyclopropyl($C_{1-3}$) alkyl, cyclopentyl, cyclopentyl($C_{1-3}$)alkyl, cyclohexyl, cyclohexyl($C_{1-3}$)alkyl, pyrrolidinyl, pyrrolidinyl($C_{1-3}$)alkyl, 1,3-dioxolanyl, 1,3-dioxolanyl($C_{1-3}$)alkyl, 2-imidazolinyl, 2-imidazolinyl($C_{1-3}$)alkyl, imidazolidinyl, imidazolidinyl ($C_{1-3}$)alkyl, 2-pyrazolinyl, 2-pyrazolinyl($C_{1-3}$)alkyl, pyrazolidinyl($C_{1-3}$)alkyl, piperidinyl, piperidinyl($C_{1-3}$)alkyl, morpholinyl, morpholinyl($C_{1-3}$)alkyl, thiomorpholinyl, thiomorpholinyl($C_{1-3}$)alkyl, piperazinyl, piperazinyl($C_{1-3}$) alkyl, piperonyl, phenyl, benzyl, phenyl($C_{2-3}$)alkyl, furyl, furyl($C_{1-3}$)alkyl, thienyl, thienyl($C_{1-3}$)alkyl, pyrrolyl($C_{1-3}$) alkyl, oxazolyl, oxazolyl($C_{1-3}$)alkyl, thiazolyl, thiazolyl ($C_{1-3}$)alkyl, imidazolyl, imidazolyl($C_{1-3}$)alkyl, pyrazolyl, pyrazolyl($C_{1-3}$)alkyl, isoxazolyl, isoxazolyl($C_{1-3}$)alkyl, isothiazolyl, isothiazolyl($C_{13}$)alkyl, 1,2,3-oxadiazolyl, 1,2,3-oxadiazolyl($C_{1-3}$)alkyl, 1,2,3-triazolyl, 1,2,3-triazolyl ($C_{1-3}$)alkyl, 1,3,4-thiadiazolyl, 1,3,4-thiadiazolyl($C_{1-3}$)alkyl, pyridinyl, pyridinyl($C_{1-3}$)alkyl, pyridazinyl, pyridazinyl ($C_{1-3}$)alkyl, pyrimidinyl, pyrimidinyl($C_{1-3}$)alkyl, pyrazinyl, pyrazinyl($C_{1-3}$)alkyl, 1,3,5-triazinyl, 1,3,5-triazinyl($C_{1-3}$) alkyl, indolyl($C_{1-3}$)alkyl, benzo[b]furyl, benzo[b]furyl($C_{1-3}$) alkyl, benzo[b]thienyl, benzo[b]thienyl($C_{1-3}$)alkyl, benzimidazolyl, benzimidazolyl($C_{1-3}$)alkyl, amino($C_{1-3}$) alkyl, $C_{1-3}$alkylamino($C_{1-3}$)alkyl, di($C_{1-3}$)alkylamino($C_{1-3}$) alkyl, aminoimino, hydroxy($C_{1-3}$)alkyl and trifluoro($C_{1-4}$) alkoxy; wherein pyrrolidinyl, 1,3-dioxolanyl, 2-imidazolinyl, imidazolidinyl, 2-pyrazolinyl, pyrazolidinyl, piperidinyl, morpholinyl, thiomorpholinyl, piperazinyl are optionally substituted with one to three substituents independently selected from the group consisting of $C_{1-4}$alkyl and oxo; and, wherein phenyl is optionally substituted with one to four substituents independently selected from the group consisting of $C_{1-4}$alkyl, $C_{1-4}$alkoxy, —OCH$_2$O—, —O(CH$_2$)$_2$O—, halogen, hydroxy and cyano; alternatively, R$^5$ and R$^6$ may, together with the nitrogen to which they are attached, form a fused heterocyclyl moiety selected from the group consisting of pyrrolidinyl, imidazolidinyl, pyrazolidinyl, piperidinyl, morpholinyl, thiomorpholinyl and piperazinyl optionally substituted with one to four substituents independently selected from $C_{1-4}$alkyl.

More preferably, R$^5$ and R$^6$ are independently selected from the group consisting of hydrogen, methyl, ethyl, n-propyl, i-propyl, t-butyl, fluoro($C_{1-3}$)alkyl, methoxy($C_{1-3}$)alkyl, methallyl, cyclopropyl, cyclohexyl, phenyl, thiazolyl, imidazolyl($C_{1-3}$)alkyl, benzimidazolyl($C_{1-3}$)alkyl, dimethylamino($C_{1-3}$)alkyl and hydroxy($C_{1-3}$)alkyl; wherein phenyl is optionally substituted with one to three substituents selected from fluorine; alternatively, R$^5$ and R$^6$ may, together with the nitrogen to which they are attached, form a fused heterocyclyl moiety selected from the group consisting of pyrrolidinyl, piperidinyl and morpholinyl optionally substituted with one to four substituents independently selected from the group consisting of methyl, ethyl, n-propyl and n-butyl.

Most preferably, R$^5$ and R$^6$ are independently selected from the group consisting of hydrogen, methyl, ethyl, n-propyl, i-propyl, t-butyl, 2-fluoroethyl, methoxyethyl, methallyl, cyclopropyl, cyclohexyl, phenyl, thiazolyl, 2-(2-imidazolyl)ethyl, benzimidazolylmethyl, dimethylaminopropyl and hydroxyethyl; wherein phenyl is optionally substituted with fluorine; alternatively, R$^5$ and R$^6$ may, together with the nitrogen to which they are attached, form a fused heterocyclyl moiety selected from the group consisting of pyrrolidinyl, piperidinyl and morpholinyl; wherein piperidinyl is substituted with two or four substituents selected from methyl.

Table 1 lists compounds exemplified in the present invention of the formula:

TABLE 1

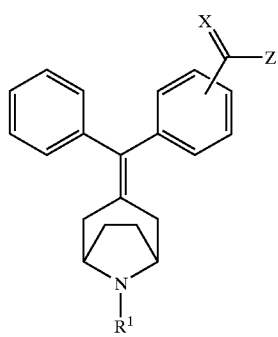

wherein the moiety —C(=X)— is substituted on phenyl at the 3 or 4 position and R$^1$, —C(=X)— and Z are dependently selected from the group consisting of:

| Ex # | R$^1$ | —X(=X)— | Z |
|---|---|---|---|
| 1 | methyl | -4-C(=O)— | N,N-diethylamino; |
| 2 | H | -4-C(=O)— | N,N-diethylamino; |
| 5 | allyl | -4-C(=O)— | N,N-diethylamino; |

TABLE 1-continued

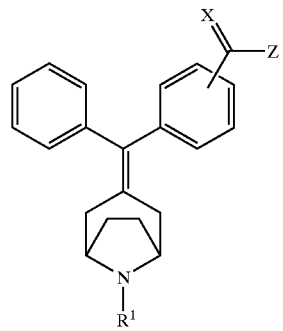

wherein the moiety —C(=X)— is substituted on phenyl at the 3 or 4 position and R$^1$, —C(=X)— and Z are dependently selected from the group consisting of:

| Ex # | R$^1$ | —X(=X)— | Z |
|---|---|---|---|
| 7 | 2-(4-fluorophenyl)ethyl | -4-C(=O)— | N,N-diethylamino; |
| 8 | 2-(2-thienyl)ethyl | -4-C(=O)— | N,N-diethylamino; |
| 9 | 2-(3-indolyl)ethyl | -4-C(=O)— | N,N-diethylamino; |
| 10 | 2-cyclohexylethyl | -4-C(=O)— | N,N-diethylamino; |
| 11 | 2-phenoxyethyl | -4-C(=O)— | N,N-diethylamino; |
| 12 | 2-(4-ethyl-5-oxo-1,4-dihydrotetrazol-1-yl)ethyl | -4-C(=O)— | N,N-diethylamino; |
| 13 | 2-phenyl-2-oxoethyl | -4-C(=O)— | N,N-diethylamino; |
| 14 | 2-(4-methyloxyphenyl)-2-oxoethyl | -4-C(=O)— | N,N-diethylamino; |
| 15 | 2-(3-cyanophenyl)-2-oxoethyl | -4-C(=O)— | N,N-diethylamino; |
| 16 | 2-(2,3-dihydro-1,4-benzodioxin-6-yl)-2-oxoethyl | -4-C(=O)— | N,N-diethylamino; |
| 17 | 2-(3,4-dihydro-2H-1,5-benzodioxepin-7-yl)-2-oxoethyl | -4-C(=O)— | N,N-diethylamino; |
| 18 | propyl | -4-C(=O)— | N,N-diethylamino; |
| 19 | 2-phenylethyl | -4-C(=O)— | N,N-diethylamino; |
| 20 | piperonyl | -4-C(=O)— | N,N-diethylamino; |
| 21 | 3-phenylpropyl | -4-C(=O)— | N,N-diethylamino; |
| 22 | methyl | -3-C(=O)— | N-methyl-N-(3-fluorophenyl)amino; |
| 25 | 2-phenylethyl | -4-C(=S)— | N,N-diethylamino; |
| 26 | 2-phenylethyl | -4-C(=O)— | N-ethylamino; |
| 29 | 2-phenylethyl | -4-C(=O)— | amino; |
| 30 | 2-phenylethyl | -4-C(=O)— | 4-morphilinyl; |
| 31 | 2-phenylethyl | -4-C(=O)— | N,N-diisopropylamino; |
| 32 | 2-phenylethyl | -4-C(=O)— | N,N-bis(methoxyethyl)amino; |
| 33 | 2-phenylethyl | -4-C(=O)— | 1-pyrrolidinyl; |
| 34 | 2-phenylethyl | -4-C(=O)— | 2,6-dimethyl-1-piperidinyl; |
| 35 | 2-phenylethyl | -4-C(=O)— | N-ethyl-N-(methylallyl)amino; |
| 36 | 2-phenylethyl | -4-C(=O)— | N,N-dipropylamino; |
| 37 | 2-phenylethyl | -4-C(=O)— | N-t-butylamino; |
| 38 | 2-phenylethyl | -4-C(=O)— | N-(2-fluoroethyl)amino; |
| 39 | 2-phenylethyl | -4-C(=O)— | N-(2-thiazolyl)amino; |
| 40 | 2-phenylethyl | -4-C(=O)— | N-(2-methyoxyethyl)amino; |
| 41 | 2-phenylethyl | -4-C(=O)— | N-(1H-benzimidazol-2-ylmethyl)amino; |
| 42 | 2-phenylethyl | -4-C(=O)— | N-cyclohexylamino; |
| 43 | 2-phenylethyl | -4-C(=O)— | N-phenylamino; |
| 44 | 2-phenylethyl | -4-C(=O)— | N-[2-(2-imidazolyl)ethyl]amino; |

TABLE 1-continued

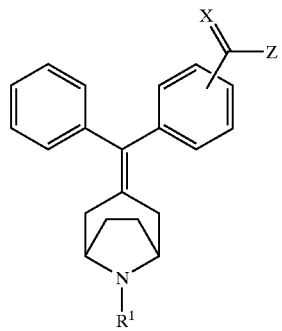

wherein the moiety —C(=X)— is substituted on phenyl at the 3 or 4 position and R¹, —C(=X)— and Z are dependently selected from the group consisting of:

| Ex # | R¹ | —X(=X)— | Z |
|---|---|---|---|
| 45 | 2-phenylethyl | -4-C(=O)— | N-cyclopropylamino; |
| 46 | 2-phenylethyl | -4-C(=O)— | N,N-(dimethylaminopropyl)amino; |
| 47 | 2-phenylethyl | -4-C(=O)— | N-ethyl-N-(hydroxyethyl)amino; |
| 48 | 2-(1,3-benzodioxol-5-yl)ethyl | -4-C(=O)— | N-ethylamino; |
| 49 | 2-(1,3-benzodioxol-5-yl)ethyl | -4-C(=O)— | N,N-diethylamino; |
| 50 | methyl | -4-C(=O)— | N-ethylamino; |
| 51 | H | -4-C(=O)— | N-ethylamino; |
| 52 | allyl | -4-C(=O)— | N-ethylamino; |
| 53 | 2-(4-methoxyphenyl)-ethyl | -4-C(=O)— | N,N-diethylamino; |
| 54 | 2-(4-methoxyphenyl)-ethyl | -4-C(=O)— | 4-morpholinyl; |
| 55 | 2-(4-methoxyphenyl)-ethyl | -4-C(=O)— | N-ethylamino; |
| 56 | 2-(4-methoxyphenyl)-ethyl | -4-C(=O)— | N,N-bis(2-methoxyethyl)amino; |
| 57 | 2-(4-methoxyphenyl)-ethyl | -4-C(=O)— | 1-pyrrolidinyl; |
| 58 | 2-(4-methoxyphenyl)-ethyl | -4-C(=O)— | 2,6-dimethyl-1-piperidinyl; |
| 59 | 2-(4-methoxyphenyl)-ethyl | -4-C(=O)— | N-ethyl-N-(methylallyl)amino; |
| 60 | 2-(4-methoxyphenyl)-ethyl | -4-C(=O)— | N,N-(di-n-propyl)amino; |
| 61 | 2-(4-methoxyphenyl)-ethyl | -4-C(=O)— | 2,2,6,6-tetramethyl-1-piperidinyl; |
| 62 | 2-(4-methoxyphenyl)-ethyl | -4-C(=O)— | N,N-(di-2-propyl)amino; |
| 69 | 2-(4-hydroxyphenyl)ethyl | -4-C(=O)— | N-ethylamino; and, |
| 70 | 2-(4-hydroxyphenyl)ethyl | -4-C(=O)— | N,N-diethylamino; | and pharmaceutically acceptable enantiomers, diastereomers and salts thereof.

Table 2 lists compounds exemplified in the present invention of the formula:

TABLE 2

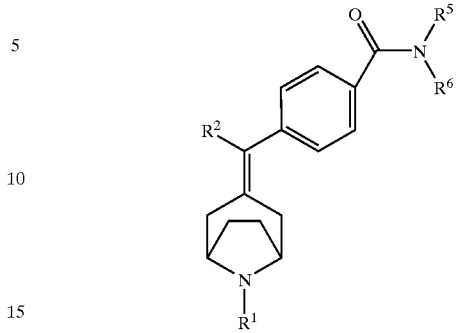

wherein R¹, R², R⁵ and R⁶ are dependently selected from the group consisting of:

| Ex # | R¹ | R² | (R⁵)(R⁶) |
|---|---|---|---|
| 63 | methyl | 4-MeOPh | (H)(Et); |
| 64 | H | 4-HOPh | (H)(Et); |
| 65 | methyl | 4-MeOPh | Et₂; |
| 66 | H | 4-HOPh | Et₂; |
| 67 | 2-(4-MeOPh)ethyl | 4-MeOPh | Et₂, and, |
| 68 | 2-(4-HOPh)ethyl | 4-HOPh | Et₂; | and pharmaceutically acceptable enantiomers, diasteromers and salts thereof.

Instant compounds of the invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharic or trifluoroacetic.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The compounds of this invention are chiral and, thus, may exist as enantiomers. In addition, the compounds may exist as diastereomers. It is to be understood that all such enantiomers and diastereomers, as well as all mixtures thereof, are encompassed within the scope of the present invention. Furthermore, some of the crystalline forms for the compounds may exist as polymorphs and as such are intended to be included in the present invention.

In addition, some of the compounds may form solvates with water (i.e., hydrates) or common organic solvents, and such solvates are also intended to be encompassed within the scope of this invention.

The present invention also contemplates a pharmaceutical composition comprising a combination of a δ-opioid or μ-opioid receptor modulator compound of Formula (I) and a μ-opioid receptor modulator compound known to those skilled in the art or a δ-opioid or μ-opioid receptor modulator compound of Formula (I) wherein the combination has a synergistic therapeutic effect.

Suitable µ-opioid receptor modulator compounds known to those skilled in the art for use in such a combination include, without limitation, the compounds alfentanil, allylprodine, alphaprodine, anileridine, bezitramide, buprenorphine, clonitazene, cyclazocine, dextromoramide, dihydrocodeine, dihydromorphine, ethoheptazine, ethylmorphine, etonitazene, fentanyl, heroin, hydromorphone, hydroxypethidine, isomethadone, ketobemidone, levallorphan, levorphanol, lofentanil, meperidine, meptazinol, metazocine, methadone, morphine, nalbuphine, norlevorphanol, normethadone, nalorphine, normorphine, opium, oxycodone, oxymorphone, phenazocine, piritramide, propiram, propoxyphene, sufentanil, tramadol and diastereomers, salts, complexes and mixtures thereof of any of the foregoing.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

The term "alkyl" refers to straight and branched-chain alkyl radical groups with 1 to 8 carbon atoms or any number within this range. The terms "alkenyl" and "alkynyl" refer to radical groups having straight and branched chains with 2 to 8 carbon atoms or any number within this range. For alkenyl chains, one double bond is formed between adjacent members of a two or three carbon chain and one or two double bonds are formed between adjacent members of a four to eight carbon chain. For alkynyl chains, one triple bond is formed between adjacent members of a two or three carbon chain and one or two triple bonds are formed between adjacent members of a four to eight carbon chain. Correspondingly, the terms "alkylene," "alkenylene" and "alkynylene" refer to alkyl, alkenyl and alkynyl linking groups wherein alkyl, alkenyl and alkynyl are as defined supra. Preferably, alkenylene and alkynylene linking group chains have at least one saturated carbon atom on each side of the unsaturated bond. More preferably, when an aryl or heteroaryl substituent is attached to the terminal carbon of an alkenylene or alkynylene linking group, at least one saturated carbon atom is between the unsaturated bond and the substituent. The term "alkoxy" refers to O-alkyl groups wherein alkyl is as defined supra.

Whenever the term "alkyl" appears in the name of a substituent (e.g., hydroxy($C_{1-6}$)alkyl) it shall be interpreted as including those limitations given above for "alkyl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "cycloalkyl" refers to branched or unbranched cyclic aliphatic hydrocarbon chains of three to seven carbon atom members. Examples of such cyclic alkyl rings include cyclopropyl, cyclobutyl, cyclopentyl, cyclohexyl or cycloheptyl.

The term "heterocyclyl" refers to a nonaromatic cyclic ring of five to seven members in which one to four members are nitrogen or a nonaromatic cyclic ring of five to seven members in which zero, one or two members are nitrogen and one member is oxygen or sulfur; and in which, a) optionally, the ring contains zero, one or two unsaturated bonds;

b) optionally, up to three carbon members adjacent to nitrogen members may be oxo substituted.

Optionally, the heterocyclyl ring is fused:

a) to a benzene ring;

b) to a 5 or 6 membered heteroaryl containing one of O, S or N and, optionally, one additional nitrogen;

c) to a 5 to 7 membered alicyclic ring;

d) to a 5 to 7 membered heterocyclyl ring of the same definition as above but absent the option of a further fused ring.

For instant compounds of the invention, the carbon atom ring members that form the heterocyclyl ring are fully saturated. Other compounds of the invention may have a partially saturated heterocyclyl ring. Preferred partially unsaturated heterocyclyl rings may have one or two double bonds. Such compounds are not considered to be fully aromatic and are not referred to as heteroaryl compounds. Therefore, a five member heterocyclyl ring may optionally have a double bond formed in the ring between adjacent ring members; a six or seven member heterocyclyl ring may have two double bonds formed in the ring between adjacent ring members.

The term aryl refers to a single aromatic ring of six carbon members or a bicyclic aromatic ring of ten carbon members. Examples of such aryl rings include phenyl and naphthyl.

The term heteroaryl refers to an aromatic ring of five or six members wherein the ring has at least one heteroatom member. Suitable heteroatoms include nitrogen, oxygen or sulfur. In the case of five-membered rings, the heteroaryl ring contains one member of nitrogen, oxygen or sulfur and, in addition, may contain up to two additional nitrogens. In the case of six-membered rings, the heteroaryl ring may contain from one to three nitrogen atoms. For the case wherein the six member ring has three nitrogens, at most two nitrogen atoms are adjacent.

The terms "halo$_{1-3}$($C_{1-8}$)alkyl," "cycloalkyl($C_{1-8}$)alkyl" or "hydroxy($C_{1-6}$)alkyl" refer to an alkylene group substituted at the terminal carbon with a halo, cycloalkyl or hydroxy group, respectively. Similarly, the term "$C_{1-8}$alkoxy($C_{1-8}$)alkenyl" or "$C_{1-8}$alkoxy($C_{1-8}$)alkynyl" refers to an alkenylene or alkynylene group substituted at the terminal carbon with an alkoxy group. The term "carbonyl" refers to the linking group —C═O—. Furthermore, the term "methylenedioxy" refers to the substituent moiety —OCH$_2$O—, the term "ethylenedioxy" refers to the substituent moiety —O(CH$_2$)$_2$O— and the term "trimethylenedioxy" refers to the substituent moiety —O(CH$_2$)$_3$O—. The term "hydroxy" refers to the group —OH and the term "oxo" refers to the group ═O. The term "halo" or "halogen" refers to the group iodine, bromine, chlorine and fluorine.

Where the compounds according to this invention are chiral, they may accordingly exist as enantiomers. In addition, the compounds may exist as diastereomers. It is to be understood that all such isomers and mixtures thereof are encompassed within the scope of the present invention.

The terms used in describing the invention are commonly used and known to those skilled in the art. As used herein, the following abbreviations have the indicated meanings:

| | |
|---|---|
| DCE | 1,2-dichloroethane |
| Et$_2$O | Diethyl ether |
| EtOH | Ethanol |
| h | Hour |
| K$_2$CO$_3$ | Potassium carbonate |
| MeOH | Methanol |
| NaBH$_4$ | Sodium borohydride |
| NaBH(OAc)$_3$ | Sodium triacetoxyborohydride |
| min | Minute |
| 2-PrOH | 2-Propanol |
| rt | Room temperature |
| TiCl$_4$ | Titanium(IV) tetrachloride |

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Scheme 1 describes a general scheme for the preparation of certain target 3-(diarylmethylene)-8-azabicyclo[3.2.1] octane derivatives of the invention using synthetic methods to prepare intermediate compounds also intended to be within the scope of the present invention.

A Suzuki reaction is used to couple a boronic acid Compound 1a with an iodinated Compound 1b in the presence of carbon monoxide to produce an intermediate Compound 1c. Alternatively, Compound 1b may also be substituted with bromine or OTF (trifluoromethylsulfonyloxy) in place of iodine. For Compound 1a and Compound 1b, the R$^2$ and R$^3$ substituents and -A-Z moiety may be varied by using appropriate starting materials or may be added in later steps.

For example, the -A- portion of the -A-Z moiety may be varied using —C(=O)— or —SO$_2$— (more preferably, —C(=O)—) and the -Z- portion of the -A-Z moiety may be varied using —OH, —O(R$^4$) or —N(R$^5$)(R$^6$) (more preferably, —O(R$^4$) or —N(R$^5$)(R$^6$)) to produce other intermediate compounds of the present invention. Similarly, target compounds wherein Z is —O(R$^4$) and R$^4$ is hydrogen may be conveniently produced by conventional hydrolysis of the Z is —N(R$^5$)(R$^6$) group; furthermore, other compounds wherein Z is —O(R$^4$) and R$^4$ is hydrogen may be esterified by conventional methods to produce other target compounds wherein R$^4$ is C$_{1-8}$alkyl.

A Robinson-Schöpf condensation is used to prepare tropinone intermediate Compounds 1e bearing an R$^1$ substituent on nitrogen by mixing an R$^1$ substituted amine Compound 1e with a succinaldehyde precursor such as 2,5-dimethoxytetrahydrofuran and acetonedicarboxylic acid. For a Compound 1e, the R$^1$ substituent may be varied by using appropriate starting materials or may be added in later steps.

Compound 1c and Compound 1e may be coupled using a titanium mediated "McMurray" reaction to produce a target Compound 1f.

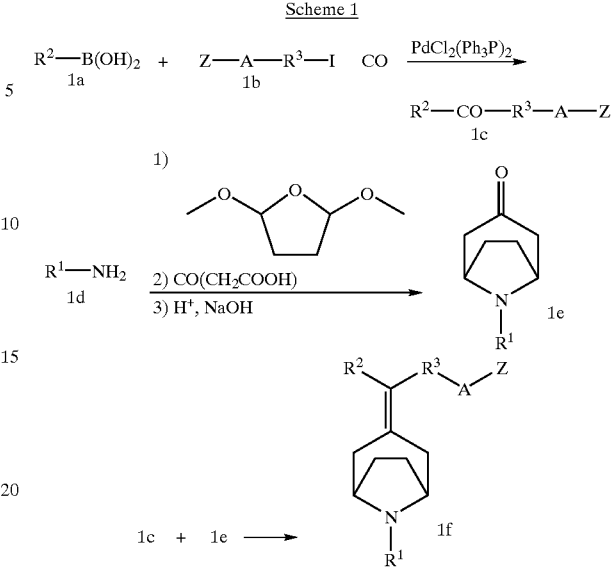

Scheme 1

Scheme 2 describes another general scheme for the preparation of certain 3-(diarylmethylene)-8-azabicyclo[3.2.1] octane derivatives.

As shown below in Scheme 2, the intermediate Compound 1c may be coupled with an 8-methyl-8-azabicyclo [3:2:1]octanone compound using titanium mediated coupling to produce an intermediate Compound 2a.

The intermediate Compound 2a may be treated with 2,2,2-trichloroethyl chloroformate followed by reflux with zinc powder in MeOH to obtain the N-demethylated Compound 2b. Compound 2c is produced by alkylation of Compound 2b with an alkyl halide or reductive alkylation with sodium triacetoxyborohydride and a carbonyl compound.

As desired, the identity of the -A-Z moiety may be varied by conversion of one -A-Z moiety to another. For example, an -A-Z moiety where the -A- portion is —C(=O)— and the -Z- portion is —O(R$^4$), the -Z- portion may be hydrolyzed to the acid, wherein —O(R$^4$) becomes —OH. Subsequently, the resulting carboxyl group may be converted to the desired amide; and, conversely, an amide group may be hydrolyzed to an acid.

Scheme 2

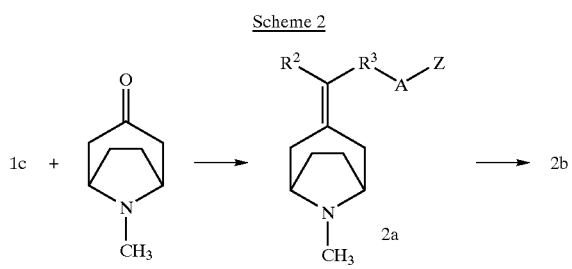

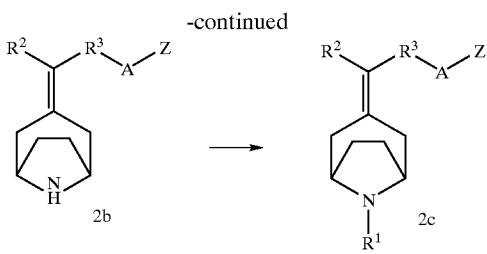

As shown in Scheme 3, a Compound 3a wherein X is O may also be further treated with a suitable thionating agent such as $P_2S_5$ or Lawesson's Reagent to prepare a Compound 3b wherein X is S.

Scheme 3

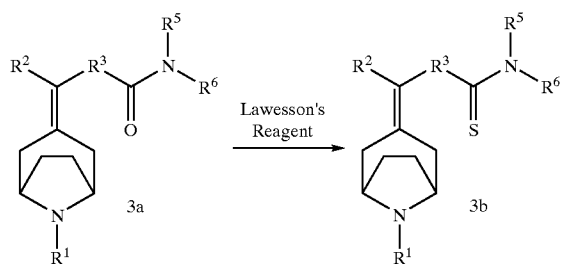

The compounds of the present invention may be used to treat mild to moderately severe pain in warm-blooded animals such as humans by administration of an analgesically effective dose. The dosage range would be from about 0.01 mg to about 15,000 mg, in particular from about 0.1 mg to about 3500 mg or, more particularly from about 0.1 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes or cluster or migraine headaches.

In regard to the use of the present compounds as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

Pharmaceutical compositions of the invention comprise the formula (I) compounds as defined above, particularly in admixture with a pharmaceutically acceptable carrier. Illustrative of the invention, therefore, is a pharmaceutical composition comprising a pharmaceutically acceptable carrier and any of the compounds described above. Another illustration of the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier.

To prepare the pharmaceutical compositions of this invention, one or more compounds of the invention or salt thereof, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Specific Synthetic Methods

Specific compounds which are representative of this invention may be prepared as per the following examples offered by way of illustration and not by way of limitation. For the sake of clarity, bracketed numbers following compound names indicate the stoichiometric salt associated with the compound, which is further exemplified by the calculated analytical data. Also, examples specifically used to prepare intermediates for the further synthesis of compounds of the invention are designated by "Procedure." As well, instant compounds may also be used as starting materials in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Procedure A

N,N-Diethyl-4-benzoylbenzamide

A solution of 25 g (110 mmol) 4-benzoylbenzoic acid [611-95-0] and 20 mL $SOCl_2$ was allowed to reflux for 2 h then allowed to cool. The excess $SOCl_2$ was evaporated off and the resulting clear oil was dissolved in 10 mL $CH_2Cl_2$ then slowly added to 12 mL (116 mmol) diethylamine in a mixture of 10 mL 3N NaOH and 50 mL $CH_2Cl_2$. The mixture was allowed to stir for 30 min then partitioned between $H_2O$ and $CH_2Cl_2$. The organic layer was washed with brine, dried over $K_2CO_3$, filtered and concentrated. The product precipitated from EtOAc/hexane to give 29.6 g (105 mmol) white crystals. MS m/z (MH$^+$) 282.

EXAMPLE 1

N,N-Diethyl-4-[(8-methyl-8-azabicyclo[3.2.1]oct-3-ylidene)phenylmethyl]benzamide Hydrochloride [1:1]

A 100 mL dry THF slurry of 18.6 g (284 mmol) zinc powder and 15.6 mL (142 mmol) $TiCl_4$ was stirred and allowed to reflux for 2 h under Ar. The reaction was allowed to cool then a 20 mL THF solution of 10 g (35.5 mmol) N,N-diethyl-4-benzoylbenzamide and 5 g (35.5 mmol) tropinone was added slowly. Once the addition was complete, the reaction was allowed to reflux for 3 h, cooled, then quenched with 10% $K_2CO_3$ in $H_2O$. The resulting slurry was partitioned between water and $Et_2O$. The organic fraction was washed with brine, dried over $MgSO_4$, filtered, and concentrated. The remaining yellow oil was absorbed onto silica gel then purified by flash chromatography eluted with 10% 0.5 M $NH_3$ in MeOH 90% $CH_2Cl_2$ to produce the product N,N-diethyl-4-[(8-methyl-8-azabicyclo[3.2.1]oct-3-ylidene)phenyl methyl] benzamide (4.27 g, 11 mmol). The HCl salt was precipitated from $Et_2O$ after the addition of ethereal HCl; mp 145–147° C. MS m/z (MH$^+$) 389. $^1$H NMR 300 MHz (DMSO-$d_6$) δ 7.2–7.45 (m, 9H), 3.8–3.9 (m, 2H), 3.15–3.25 (m, 2H), 2.75–2.95 (m, 4H), 2.65 (s, 3H), 2.25–2.4 (m, 2H), 2.15–2.25 (m, 2H), 1.75–1.9 (m, 2H), 0.95–1.2 (m, 6H). Anal calc $C_{26}H_{32}N_2O\cdot HCl$ (3% $H_2O$): C, 71.21; H, 7.93; N, 6.39. Found: C, 71.16; H, 7.95; N, 6.27.

EXAMPLE 2

N,N-Diethyl-4-[(8-azabicyclo[3.2.1]oct-3-ylidene)phenylmethyl]benzamide Hydrochloride [1:1]

A 100 mL benzene suspension of 3.1 g (5.6 mmol) N,N-diethyl-4-[(8-methyl-8-azabicyclo[3.2.1]oct-3-ylidene)phenylmethyl]benzamide, 3.45 g (25 mmol) $K_2CO_3$, and 1.5 mL (10 mmol) 2,2,2-trichloroethyl chloroformate was allowed to reflux for 2 h. The reaction was cooled, filtered, and the solvent evaporated. The residual oil was dissolved in MeOH then stirred at reflux with 2.6 g (40 mmol) zinc powder for 1 h. After cooling, the reaction was filtered through celite and partitioned between 3N NaOH and $CH_2Cl_2$. The organic layer was washed with brine, dried over $K_2CO_3$, filtered, and concentrated (2.1 g, 5.6 mmol). The resulting clear oil was dissolved in $Et_2O$, filtered, and the product precipitated after the addition of ethereal HCl; mp 128–132° C. MS m/z (MH$^+$) 375. $^1$H NMR 300 MHz (DMSO-$d_6$) δ 7.15–7.4 (m, 9H), 3.9–4.0 (m, 2H), 3.15–3.3 (m, 2H), 2.55–2.65 (m, 2H), 2.25–2.35 (m, 4H), 1.9–2.0 (m, 2H), 1.75–1.85 (m, 2H), 1.0–1.2 (m, 6H). Anal calc $C_{25}H_{30}N_2O\cdot HCl$ (3% $H_2O$): C, 70.89; H, 7.71; N, 6.61. Found: C, 70.52; H, 7.41; N, 6.24.

EXAMPLE 3

(+)-N,N-Diethyl-4-[[(1R,5S)-8-azabicyclo[3.2.1]oct-3-ylidene]phenylmethyl]benzamide Fumarate [1:1]

N,N-Diethyl-4-[(8-azabicyclo[3.2.1]oct-3-ylidene)phenylmethyl]benzamide was chromatographed on a CHIRALPAK® AS™ eluting with 90:9.9:0.1 acetonitrile:2-propanol:diethylamine. The first enantiomer to elute was converted to its fumarate salt in 2-PrOH. $[\alpha]_D^{25}$=+29°. MS m/z (MH$^+$) 375.

EXAMPLE 4

(−)-N,N-Diethyl-4-[[(1R,5S)-8-azabicyclo[3.2.1]oct-3-ylidene]phenylmethyl]benzamide Fumarate [1:1]

The second enantiomer to elute in the chromatography from the foregoing example was collected. $[\alpha]_D^{25}$=−22°. MS m/z (MH$^+$) 375.

EXAMPLE 5

N,N-Diethyl-4-[(8-allyl-8-azabicyclo[3.2.1]oct-3-ylidene)phenylmethyl]benzamide Hydrochloride [1:1]

A 20 mL acetonitrile suspension of 0.4 g (1.0 mmol) N,N-diethyl-4-[(8-azabicyclo[3.2.1]oct-3-ylidene)phenylmethyl]benzamide, 0.4 g (3.0 mmol) $K_2CO_3$, and 0.09 mL allyl bromide was allowed to stir for 3 h. The reaction was filtered and concentrated. The remaining oil was absorbed onto silica gel then purified by flash chromatography eluted with 5% 0.5 M $NH_3$ in MeOH 95% $CH_2Cl_2$. The pure product (0.2 g, 0.4 mmol) was taken up in $Et_2O$, filtered, and precipitated after the addition of ethereal HCl. MS m/z (MH$^+$) 415. $^1$H NMR 300 MHz (DMSO-$d_6$) δ 7.15–7.45 (m, 9H), 5.95–6.10 (m, 1H), 5.4–5.55 (m, 2H), 3.85–3.95 (m, 2H), 3.55–3.65 (t, 2H), 3.35–3.45 (m, 2H), 3.1–3.25 (m, 2H), 2.75–2.85 (t, 2H), 2.2–2.3 (m, 2H), 2.1–2.25 (m, 2H), 1.75–1.9 (m, 2H), 1.0–1.2 (m, 6H).

EXAMPLE 6

(−)-N,N-Diethyl-4-[[(1R,5S)-8-allyl-8-azabicyclo[3.2.1]oct-3-ylidene]phenylmethyl]benzamide Hydrochloride Following the protocol for Example 5 and substituting (+)-N,N-diethyl-4-[[(1R,5S)-8-azabicyclo[3.2.1]oct-3-ylidene]phenylmethyl]benzamide for N,N-diethyl-4-[(8-azabicyclo[3.2.1]oct-3-ylidene)phenylmethyl]benzamide the title compound was obtained: MS m/z (MH$^+$) 415. $[\alpha]_D^{25}$=−3.8°. $^1$H NMR 300 MHz (DMSO-$d_6$) δ 7.15–7.45 (m, 9H), 5.95–6.10 (m, 1H), 5.4–5.55 (m, 2H), 3.85–3.95 (m, 2H), 3.55–3.65 (t, 2H), 3.35–3.45 (m, 2H), 3.1–3.25 (m, 2H), 2.75–2.85 (t, 2H), 2.2–2.3 (m, 2H), 2.1–2.25 (m, 2H), 1.75–1.9 (m, 2H), 1.0–1.2 (m, 6H).

EXAMPLES 7–17

N,N-Diethyl-4-[(8-R$^1$-8-azabicyclo[3.2.1]oct-3-ylidene)phenylmethyl]benzamides Following the procedure of Example 5 and substituting the appropriate alkyl bromide for allyl bromide the following compounds were prepared:

| Ex# | Alkyl bromide | R$^1$ | MS m/z (MH$^+$) |
|---|---|---|---|
| 7 | 2-(4-fluorophenyl)ethyl bromide | 2-(4-fluorophenyl)ethyl | 497 |

-continued

| Ex# | Alkyl bromide | R$^1$ | MS m/z (MH$^+$) |
|---|---|---|---|
| 8 | 2-(2-thienyl)ethyl bromide | 2-(2-thienyl)ethyl | 485 |
| 9 | 3-(2-bromoethyl)indole | 2-(3-indolyl)ethyl | 518 |
| 10 | 1-bromo-2-cyclohexylethane | 2-cyclohexylethyl | 485 |
| 11 | 2-phenoxyethyl bromide | 2-phenoxyethyl | 495 |
| 12 | 1-(bromoethyl)-4-ethyl-1,4-dihydrotetrazol-5-one | 2-(4-ethyl-5-oxo-1,4-dihydrotetrazol-1-yl)ethyl | 515 |
| 13 | 2-bromo-1-phenylethanone | phenylcarbonylmethyl | 493 |
| 14 | 2-bromo-1-(4-methoxyphenyl)ethanone | (4-methoxyphenyl)carbonylmethyl | 523 |
| 15 | 2-bromo-1-(3-cyanophenyl)ethanone | (3-cyanophenyl)carbonylmethyl | 518 |
| 16 | 2-bromo-1-[3,4-(ethylenedioxy)phenyl]ethanone | 3,4-(ethylenedioxy phenyl)carbonylmethyl | 551 |
| 17 | 2-bromo-1-[3,4-(trimethylenedioxy)phenyl]-ethanone | 3,4-(trimethylenedioxy phenyl)carbonylmethyl | 565 |

EXAMPLE 18

N,N-Diethyl-4-[(8-propyl-8-azabicyclo[3.2.1] oct-3-ylidene)phenylmethyl]benzamide Hydrochloride [1:1]

A slurry of 0.4 g (1.0 mmol) N,N-diethyl-4-[(8-azabicyclo[3.2.1]oct-3-ylidene)phenylmethyl]benzamide, 0.11 mL (1.5 mmol) propionaldehyde, 0.1 mL (1.7 mmol) HOAc, and 0.5 g (2.3 mmol) NaBH(OAc)$_3$ in 20 mL DCE was allowed to stir for 16 h. The reaction was made strongly basic with 3N NaOH and diluted with CH$_2$Cl$_2$. The organic layer was separated, washed with brine, dried over K$_2$CO$_3$, filtered, and concentrated. The remaining oil was absorbed onto silica gel and purified by flash chromatography eluted with 5% 0.5 M NH$_3$ in MeOH 95% CH$_2$Cl$_2$. The pure product (0.25 g, 0.6 mmol) was taken up in Et$_2$O, filtered, and precipitated after the addition of ethereal HCl; mp 184–184° C. MS m/z (MH$^+$) 417. $^1$H NMR 300 MHz (CD$_3$OD) δ 7.2–7.45 (m, 9H), 3.95–4.05 (m, 2H), 3.45–3.6 (m, 2H), 3.2–3.3 (m, 2H), 2.95–3.05 (m, 2H), 2.55–2.7 (m, 4H), 2.2–2.3 (m, 2H), 1.95–2.05 (m, 2H), 1.7–1.85 (m, 2H), 1.0–1.35 (br m, 9H). Anal calc C$_{28}$H$_{36}$N$_2$O HCl.0.5H$_2$O: C, 72.78; H, 8.29; N, 6.06. Found: C, 73.01; H, 7.94; N, 5.85.

EXAMPLES 19–21

N,N-Diethyl-4-[(8-R$^1$-8-azabicyclo[3.2.1]oct-3-ylidene)phenylmethyl]benzamides Following the procedure of Example 18 and substituting the appropriate carbonyl compound for propionaldehyde the following compounds were prepared:

| Ex# | Carbonyl Compound | R$^1$ | MS m/z (MH$^+$) |
|---|---|---|---|
| 19 | phenylacetaldehyde | 2-phenylethyl | 479 |
| 20 | piperonal | piperonyl | 509 |
| 21 | hydrocinnamaldehyde | 3-phenylpropyl | 493 |

Procedure B

N-(3-Fluorophenyl)-N-methyl-3-benzoylbenzamide

Following Procedure A with the substitution of 20 g (88 mmol) 3-benzoylbenzoic acid [579-18-0] and 8.5 mL (88 mmol) 3-fluoroaniline for 4-benzoylbenzoic acid and diethyl amine, the product N-(3-fluorophenyl)-3-benzoylbenzamide was generated (28 g, 88 mmol) as a clear oil. The oil was dissolved in 50 mL dry THF to which a 10 mL THF slurry of 2.1 g (90 mmol) NaH was slowly added. The mixture was allowed to stir for 5 min then 5.6 mL (90 mmol) of MeI was added and continued stirring for 16 h. The reaction was carefully quenched with water and partitioned between water and CH$_2$Cl$_2$. The organic layer was washed with brine, dried over K$_2$CO$_3$, filtered, and concentrated to yield 29.3 g (88 mmol) product. MS m/z (MH$^+$) 334.

EXAMPLE 22

N-(3-Fluorophenyl)-N-methyl-3-[(8-methyl-8-azabicyclo[3.2.1]oct-3-ylidene)phenylmethyl] benzamide Fumarate [1:1]

Following the procedure of Example 1 with the substitution of N-(3-fluorophenyl)-N-methyl-3-benzoylbenzamide obtained in Procedure B for N,N-diethyl-4-benzoylbenzamide, the product N-(3-fluorophenyl)-N-methyl-3-[(8-methyl-8-azabicyclo[3.2.1]oct-3-ylidene) phenylmethyl]benzamide was produced. The fumarate salt was precipitated from 2-PrOH/hexane, mp 122–125° C. MS m/z (MH$^+$) 441. $^1$H NMR 300 MHz (DMSO-d$_6$) δ 6.85–7.35 (m, 13H), 3.4 (s, 3H), 3.3–3.5 (m, 1H), 3.15–3.2 (m, 1H), 3.4–3.55 (m, 2H), 2.35 (s, 3H), 2.15–2.25 (m, 1H), 2.05–2.15 (m, 1H), 1.9–2.05 (m, 2H), 1.55–1.65 (m, 1H), 1.35–1.55 (br ms, 1H). Anal calc C$_{29}$H$_{29}$FN$_2$O.C$_4$H$_4$O$_4$: C, 71.21; H, 5.98; N, 5.03. Found: C, 71.50; H, 6.20; N, 4.92.

EXAMPLE 23

(−)-N,N-Diethyl-4-[[(1R,5S)-8-phenethyl-8-azabicyclo[3:2:1]oct-3-ylidene]phenylmethyl] benzamide Hydrochloride [1:1]

A suspension of 52 g (0.8 mole) of zinc powder and 800 mL of THF was cooled in an ice bath 44 mL (0.4 mole) of TiCl$_4$ was added dropwise with stirring. The ice bath was removed and the reaction refluxed for 2 h. A solution of 26.45 g (0.094 mole) of N,N-diethyl-4-benzoylbenzamide and 23.9 g (0.094 mole) of 8-phenethyl-8-azabicyclo[3.2.1] octan-3-one, in 100 mL of THF was added dropwise and the reaction was refluxed 4 h. After cooling, the reaction mixture was poured into a beaker containing excess K$_2$CO$_3$ and ice. The mixture was extracted with ether, washed with brine, dried (K$_2$CO$_3$) and concentrated. There was obtained 47 g (~0.1 mol) of crude (±)-N,N-diethyl-4-[(8-phenethyl-8-azabicyclo[3:2:1]oct-3-ylidene)phenylmethyl]benzamide as an oil. A sample of the oil and 38.33 g (0.1 mole) of (+)-ditoluoyl-D-tartaric acid were combined in 600 mL of acetonitrile. The solid was collected and recrystallized twice from acetonitrile. The solid was collected and partitioned between dilute sodium hydroxide and CH$_2$Cl$_2$. The organic solution was dried (K$_2$CO$_3$) and concentrated. The residue was converted to a hydrochloride salt (Et$_2$O/HCl). It was recrystallized from 2-PrOH to give 5.6 g of white solid. Et$_2$O, filtered, and precipitated after the addition of ethereal HCl; mp 210–211° C. MS m/z (MH$^+$) 479. $^1$H NMR 300 MHz (CDCl$_3$) δ 12.6 (s, 1H), 7.2–7.45 (m, 14H), 3.85 (S, 2H), 3.5–3.1 (m, 10H), 2.6 (d, 1H), 2.5 (d, 2H), 2.05 (m, 2H), 1.2 (br. s, 3H), 1.1 (br. s, 3H). [α]$_D^{25}$=−3.7°.

EXAMPLE 24

(+)-N,N-Diethyl-4-[[(1S,5R)-8-phenethyl-8-azabicyclo[3:2:1]oct-3-ylidene]phenylmethyl] benzamide Hydrochloride [1:1]

The mother liquors from the foregoing example were concentrated and partitioned between dilute sodium hydroxide and CH$_2$Cl$_2$. The organic solution was concentrated (40.5 g, 0.084 mole) and 32.7 g (0.084 mole) of (−)-ditoluoyl-L-tartaric acid were combined in 500 mL of acetonitrile. The solid was collected and recrystallized twice from acetonitrile. The solid was collected and partitioned between dilute sodium hydroxide and CH$_2$Cl$_2$. The organic solution was dried (K$_2$CO$_3$) and concentrated. The residue was converted to a hydrochloride salt (Et$_2$O/HCl) and recrystallized from 2-PrOH to give a white solid; mp 211–212° C. MS m/z (MH$^+$) 479. $^1$H NMR 300 MHz (CDCl$_3$) δ 12.6 (s, 1H), 7.2–7.45 (m, 14H), 3.85 (S, 2H), 3.5–3.1 (m, 10H), 2.6 (d, 1H), 2.5 (d, 2H), 2.05 (m, 2H), 1.2 (br. s, 3H), 1.1 (br. s, 3H). $[α]_D^{25}$=+3.7°.

EXAMPLE 25

(−)-N,N-Diethyl-4-[[8-phenethyl-8-aza(1R, 5S) bicyclo[3:2:1]oct-3-ylidene]phenylmethyl] thiobenzamide A mixture of 1.48 g (3.1 mmol) of (−)-N,N-diethyl-4-[[8-phenethyl-8-aza(1R, 5S)bicyclo[3:2:1]oct-3-ylidene] phenylmethyl]benzamide and 1.87 g of Lawesson's reagent was heated at 60° C. in 50 mL of benzene for 2 h. The resulting mixture was flash chromatographed using 5% MeOH in CH$_2$Cl$_2$. MS m/z (MH$^+$) 495. $^1$H NMR 300 MHz (CDCl$_3$) δ 8.2 (m, 2H), 7.3–7.0 (m, 10H), 6.8 (m, 2H) 4.0 (m, 4H), 3.7–3.2 (m, 10H), 2.7–2.4 (m, 3H), 2.1–1.6 (m, 4H), 1.4 (t, 3H), 1.1 (t, 3H).

Procedure C

Ethyl 4-[(8-phenethyl-B-azabicyclo[3.2.1]oct-3-ylidene)phenylmethyl]benzoate

After a mixture of 52 g (0.8 mole) of zinc powder and 800 mL of THF was cooled in an ice bath 44 mL (0.4 mole) of TiCl$_4$ was added dropwise with stirring. The ice bath was removed and the reaction refluxed for 2 h. A solution of 21.5 g (0.094 mole) of ethyl 4-benzoylbenzoate, 23.9 g (0.094 mole) of 8-phenethyl-8-azabicyclo[3.2.1]octan-3-one, in 100 mL of THF was added dropwise and the reaction was refluxed overnight. After cooling the reaction mixture was poured into a beaker containing K$_2$CO$_3$ and ice. Enough K$_2$CO$_3$ was added until basic. The solid was filtered off and the organics from the filtrate were separated. The aqueous layer was extracted with Et$_2$O and the organics were combined, washed with brine and dried over K$_2$CO$_3$. The solvent was evaporated in vacuo. The residue was first passed through a flash column, silica gel, (9:1; CH$_2$Cl$_2$:MeOH) then a second column using silica gel with 3:1 hexane:acetone to give 21.8 g of the title compound. MS m/z (MH$^+$) 452. $^1$H NMR (DMSO-d$_6$) δ 8.0 (d, 2H); 7.35–7.1 (Ar, 12H); 4.3 (t, 2H); 2.8 (m, 2H); 2.7 (m, 2H); 2.4 (bd, 2H); 2.3–2.2 (m, 3H); 1.9 (m, 2H); 1.6 (m, 3H); 1.3 (q, 3H).

Procedure D

4-[(8-Phenethyl-8-azabicyclo[3.2.1] oct-3-ylidene) phenylmethyl]benzoic Acid

A mixture of 22 g (0.048 mole) of ethyl 4-[(8-phenethyl-8-azabicyclo[3.2.1]oct-3-ylidene)phenylmethyl]benzoate, 86 mL of 3N NaOH and 200 mL of EtOH was refluxed for 1 h. After cooling the mixture was made acidic with conc. HCl. The solvent was decanted away from the gum which formed. The gum was titurated with Et$_2$O and Et$_2$O/HCl and was placed into a drying oven overnight at 45° C. to yield 19.2 g of 4-[(8-phenethyl-8-azabicyclo[3.2.1]oct-3-ylidene) phenylmethyl]benzoic acid; mp. 285–290° C. MS m/z (MH$^+$) 425. $^1$H NMR δ 7.9 (d, 2H); 7.4–7.2 (ar, 12H); 3.7 (bs, 2H); 3.0 (bs, 4H); 2.8 (bd, 2H); 2.2 (t, 2H); 2.0 (m, 2H); 1.65 (m, 2H).

Procedure E

4-[(8-Phenethyl-8-azabicyclo[3.2.1]oct-3-ylidene) phenylmethyl]benzoyl Chloride

A mixture of 6 g (0.014 mole) of 4-[(8-phenethyl-8-azabicyclo[3.2.1]oct-3-ylidene)phenylmethyl]benzoic acid, 20 ml of CHCl$_2$ and 3 mL (0.042 mole) of thionyl chloride were refluxed for 1.5 h. The solvent was evaporated in vacuo to give 6.2 g of 4-[(8-phenethyl-8-azabicyclo[3.2.1]oct-3-ylidene)phenylmethyl]benzoyl chloride. MS m/z (MH$^+$) of CH$_3$OH quench 437.

EXAMPLE 26

N-Ethyl-4-[(8-phenethyl-8-azabicyclo[3.2.1]oct-3-ylidene)phenylmethyl]benzamide

A mixture of 11.4 g (0.14 mole) of ethylamine hydrochloride and 150 mL of 3N NaOH and 100 mL of CH$_2$Cl$_2$ were cooled in an ice bath. A solution of 4.7 g (0.015 mole) of 4-[(8-phenethyl-8-azabicyclo[3.2.1]oct-3-ylidene) phenylmethyl]benzoyl chloride prepared using Procedure E in 60 mL of CH$_2$Cl$_2$ was added. After the addition was complete, the ice bath was removed and the reaction stirred at room temperature for 2 h. The organics were separated off and washed with water, brine and dried (K$_2$CO$_3$). The solvent was evaporated in vacuo and converted to the HCl salt with Et$_2$O/HCl to give 1.86 g of N-ethyl-4-[(8-phenethyl-8-azabicyclo[3.2.1]oct-3-ylidene)phenylmethyl] benzamide; mp 296–298° C. (Decomp). MS m/z (MH$^+$) 451. $^1$H NMR (DMSO-d$_6$) δ 8.5 (ar, 1H); 7.8 (d, 2H); 7.4–7.1 (ar, 12H); 4.05 (bs, 2H); 3.4–3.2 (m, 3H); 3.1 (s, 3H); 2.9 (d, 2H); 2.4 –2.1 (m, 4H); 1.8 (m, 2H); 1.1 (t, 3H).

EXAMPLE 27

(−)-4-[[8-Phenethyl-8-aza(1R,5S)bicyclo[3.2.1] oct-3-ylidene]phenylmethyl]benzamide 4-[[8-Phenethyl-8-aza(1R,5S)bicyclo[3.2.1]oct-3-ylidene]phenylmethyl]benzamide was chromatographed on a CHIRALPAK® Ad™ column eluting with EtOH+0.1% dea. The first enantiomer to elute was collected and converted to the hydrochloride with Et$_2$O/HCl. $[α]_D^{25}$=−9.7°. MS m/z (MH$^+$) 451. $^1$H NMR (DMSO-d$_6$) δ 8.5 (ar, 1H); 7.8 (d, 2H); 7.4–7.1 (ar, 12H); 4.05 (bs, 2H); 3.4–3.2 (m, 3H); 3.1 (s, 3H); 2.9 (d, 2H); 2.4 –2.1 (m, 4H); 1.8 (m, 2H); 1.1 (t, 3H).

EXAMPLE 28

(+)-4-[[8-Phenethyl-8-aza(1S,5R)bicyclo[3.2.1]oct-3-ylidene]phenylmethyl]benzamide The second enantiomer to elute was collected and converted to the hydrochloride with Et$_2$O/HCl. $[α]_D^{25}$=−9.3°. MS m/z (MH$^+$) 451. $^1$H NMR (DMSO-d$_6$) δ 8.5 (ar, 1H); 7.8 (d, 2H); 7.4–7.1 (ar, 12H); 4.05 (bs, 2H); 3.4–3.2 (m, 3H); 3.1 (s, 3H); 2.9 (d, 2H); 2.4 –2.1 (m, 4H); 1.8 (m, 2H); 1.1 (t, 3H).

EXAMPLE 29

4-[(8-Phenethyl-8-azabicyclo[3.2.1]oct-3-ylidene) phenylmethyl]benzamide Hydrochloride [1:1]

A 1.5 g (0.0034 mole) sample of 4-[(8-phenethyl-8-azabicyclo[3.2.1]oct-3-ylidene)phenylmethyl]benzoyl chloride was cooled in an ice bath. 30 mL of NH$_4$OH was added dropwise. The ice bath was removed and the mixture was stirred at room temperature for 2 h. The solid was filtered off and dried. The product was passed through a Biotage Flash 40 L (silica gel, 9:1; CH$_2$Cl$_2$:MeOH). Conversion to the HCl salt and recrystallization from EtOH/Et$_2$O gave 0.45 g of 4-[(8-phenethyl-8-azabicyclo[3.2.1]oct-3-ylidene) phenylmethyl]benzamide; mp. 210–212° C. MS m/z (MH$^+$) 423. $^1$H NMR (DMSO-d$_6$) δ 7.95 (s, 1H); 7.9 (d, 2H); 7.4–7.2 (ar, 12H); 4.05 (bs, 1H); 3.6 (q, 2H); 2.9 (d, 2H); 2.4–2.1 (m, 5H); 1.8 (m, 3H); 1.1 (t, 3H).

EXAMPLES 30–47

N,N-R$^2$,R$^3$-4-[(8-Phenethyl-8-azabicyclo[3.2.1]oct-3-ylidene)phenylmethyl]benzamides By the method of Example 26 and substituting the appropriate amine for ethylamine hydrochloride, the title compound was prepared.

| Ex | Amine | CIMS (MH$^+$) |
| --- | --- | --- |
| 30 | morpholine | 493 |
| 31 | diisopropylamine | 506 |
| 32 | bis(methoxyethyl)amine | 538 |
| 33 | pyrrolidine | 477 |
| 34 | cis-2,6-dimethylpiperidine | 519 |
| 35 | N-ethyl-N-(methylallyl)amine | 505 |
| 36 | dipropylamine | 507 |
| 37 | t-butylamine | 479 |
| 38 | 2-fluoroethylamine | 469 |
| 39 | 2-aminothiazole | 507 |
| 40 | 2-methoxyethylamine | 481 |
| 41 | (1H-benzimidazol-2-ylmethyl)amine | 553 |
| 42 | cyclohexylamine | 505 |
| 43 | aniline | 499 |
| 44 | histamine | 517 |
| 45 | cyclopropylamine | 463 |
| 46 | N,N-(dimethylaminopropyl)amine | 508 |
| 47 | N-ethyl-N-(hydroxyethyl)amine | 495 |

Procedure F 8-(2-Benzo[1,3]dioxol-5-ylethyl)-8-azabicyclo [3.2.1]octan-3-one

A 41 g of 2,5-dimethoxytetrahydrofuran (0.32 ml) was suspended in 300 mL of H$_2$O and 40 mL of o-phosphoric acid was added. The mixture was stirred for 3 h then brought to pH 7 by addition of 3N NaOH. Samples of acetone dicarboxylic acid (51 g, 0.15 mol) and (3,4-methylenedioxy) phenethylamine (20 g, 0.12 mol) were added and the mixture stirred at 25° C. for two days. The mixture was made basic by addition of 100 mL of 3N NaOH, was extracted with EtOAc, washed with brine, dried (K$_2$CO$_3$) and concentrated. The residue was flash chromatographed using 20% acetone in hexane. The product was a crystalline solid. MS m/z (MH$^+$) 274. $^1$H NMR 300 MHz (CDCl$_3$) δ 6.6 (m, 3H), 5.9 (s, 2H), 3.5 (br. m, 2H), 2.85 (s, 4H), 2.65 (dd, 2H), 2.2 (d, 2H), 2.05 (m, 2H), 1.7 (q, 2H).

Procedure G

Ethyl [[8-(2-benzo[1,3]dioxol-5-ylethyl)-8-azabicyclo[3:2:1]oct-3-ylidene]phenylmethyl] benzoate Following the protocol of Procedure C and substituting 8-(2-benzo[1,3]dioxol-5-ylethyl)-8-azabicyclo[3.2.1]octan-3-one for 8-phenethyl-8-azabicyclo[3.2.1]octan-3-one, the title compound was obtained. MS m/z (MH$^+$) 496.

Procedure H

[[8-(2-Benzo[1,3]dioxol-5-ylethyl)-8-azabicyclo [3:2:1]oct-3-ylidene]phenylmethyl]benzoic Acid Following the protocol of Procedure D and substituting ethyl-[[8-(2-benzo[1,3]dioxol-5-ylethyl)-8-azabicyclo [3:2:1]oct-3-ylidene]phenylmethyl]benzoate for ethyl-4-[(8-phenethyl-8-azabicyclo[3.2.1]oct-3-ylidene)phenylmethyl] benzoate, the title compound was obtained. MS m/z (MH$^+$) 468.

Procedure J

[[8-(2-Benzo[1,3]dioxol-5-ylethyl)-8-azabicyclo [3:2:1]oct-3-ylidene]phenylmethyl]benzoyl Chloride Following the protocol of Procedure E and substituting [[8-(2-benzo[1,3]dioxol-5-ylethyl)-8-azabicyclo[3:2:1]oct-3-ylidene]phenylmethyl]benzoic acid for 4-[(8-phenethyl-8-azabicyclo[3.2.1]oct-3-ylidene)phenylmethyl]benzoic acid, the title compound was obtained.

EXAMPLE 48

N-Ethyl-[[8-(2-Benzo[1,3]dioxol-5-ylethyl)-8-azabicyclo[3:2:1]oct-3-ylidene]phenylmethyl] benzamide Following the procedure of Example 23 and substituting [[8-(2-benzo[1,3]dioxol-5-ylethyl)-8-azabicyclo[3:2:1]oct-3-ylidene]phenylmethyl]benzoyl chloride for 4-[(8-phenethyl-8-azabicyclo[3.2.1]oct-3-ylidene)phenylmethyl] benzoyl chloride, the title compound was obtained. MS m/z (MH$^+$) 495.

EXAMPLE 49

N,N-Diethyl-[[8-(2-Benzo[1,3]dioxol-5-ylethyl)-8-azabicyclo[3:2:1]oct-3-ylidene]phenylmethyl] benzamide Following the procedure of Example 23 and substituting [[8-(2-benzo[1,3]dioxol-5-ylethyl)-8-azabicyclo[3:2:1]oct-3-ylidene]phenylmethyl]benzoyl chloride for 4-[(8-phenethyl-8-azabicyclo[3.2.1]oct-3-ylidene)phenylmethyl] benzoyl chloride and diethyl amine for ethylamine hydrochloride, the title compound was obtained. MS m/z (MH$^+$) 523.

Procedure K

Ethyl 4-[(8-methyl-8-azabicyclo[3.2.1]oct-3-ylidene)phenylmethyl]benzoate

Following the protocol of Procedure C and substituting tropinone for 8-phenethyl-8-azabicyclo[3.2.1]octan-3-one, the title compound was obtained. MS m/z (MH$^+$) 362.

Procedure L

4-[(8-Methyl-8-azabicyclo[3.2.1]oct-3-ylidene) phenylmethyl]benzoic Acid

Following the protocol of Procedure D and substituting ethyl 4-[(8-methyl-8-azabicyclo[3.2.1]oct-3-ylidene) phenylmethyl]benzoate for ethyl 4-[(8-phenethyl-8-azabicyclo[3.2.1]oct-3-ylidene)phenylmethyl]benzoate, the title compound was obtained. MS m/z (MH$^+$) 334

Procedure M

4-[(8-Methyl-8-azabicyclo[3.2.1]oct-3-ylidene)phenylmethyl]benzoyl Chloride

Following the protocol of Procedure E and substituting 4-[(8-methyl-8-azabicyclo[3.2.1]oct-3-ylidene)phenylmethyl]benzoic acid for 4-[(8-phenethyl-8-azabicyclo[3.2.1]oct-3-ylidene)phenylmethyl]benzoic acid, the title compound was obtained.

EXAMPLE 50

N-Ethyl-4-[(8-Methyl-8-azabicyclo[3.2.1]oct-3-ylidene)phenylmethyl]benzamide Following the protocol of Example 26 and substituting 4-[(8-methyl-8-azabicyclo[3.2.1]oct-3-ylidene)phenylmethyl]benzoyl chloride for 4-[(8-phenethyl-8-azabicyclo[3.2.1]oct-3-ylidene)phenylmethyl]benzoyl chloride, the title compound was obtained. MS m/z (MH$^+$) 361.

EXAMPLE 51

N-Ethyl-4-[(8-azabicyclo[3.2.1]oct-3-ylidene)phenylmethyl]benzamide

Following the protocol of Example 2 and substituting N-ethyl-4-[(8-methyl-8-azabicyclo[3.2.1]oct-3-ylidene)phenylmethyl]benzamide for N,N-diethyl-4-[(8-methyl-8-azabicyclo[3.2.1]oct-3-ylidene)phenylmethyl]benzamide, the title compound was obtained. MS m/z (MH$^+$) 347.

EXAMPLE 52

N-Ethyl-4-[(8-allyl-8-azabicyclo[3.2.1]oct-3-ylidene)phenylmethyl]benzamide

Following the protocol of Example 6 and substituting N-ethyl-4-[(8-azabicyclo[3.2.1]oct-3-ylidene)phenylmethyl]benzamide for N,N-diethyl-4-[(8-azabicyclo[3.2.1]oct-3-ylidene)phenylmethyl]benzamide, the title compound was obtained. MS m/z (MH$^+$) 387.

Procedure N

8-[2-(4-Methoxyphenyl)ethyl]-8-azabicyclo[3:2:1]octanone

Following the protocol of Procedure F and substituting (4-methoxy)phenethylamine for (3,4-methylenedioxy)phenethylamine, the title compound was obtained. MS m/z (MH$^+$) 260.

Procedure O

Ethyl 4-[[8-[2-(4-methoxyphenyl)ethyl]-8-azabicyclo[3:2:1]oct-3-ylidene]phenylmethyl]benzoate Following the protocol of Procedure C and substituting 8-[2-(4-methoxyphenyl)ethyl]-8-azabicyclo[3:2:1]octanone for 8-phenethyl-8-azabicyclo[3.2.1]octan-3-one, the title compound was obtained. MS m/z (MH$^+$) 482.

Procedure P

4-[[8-[2-(4-Methoxyphenyl)ethyl]-8-azabicyclo[3:2:1]oct-3-ylidene]phenylmethyl]benzoic Acid Following the protocol of Procedure D and substituting ethyl 4-[[8-[2-(4-methoxyphenyl)ethyl]-8-azabicyclo[3:2:1]oct-3-ylidene]phenylmethyl]benzoate for ethyl 4-[(8-phenethyl-8-azabicyclo[3.2.1]oct-3-ylidene)phenylmethyl]benzoate, the title compound was obtained.

Procedure Q

4-[[8-[2-(4-Methoxyphenyl)ethyl]-8-azabicyclo[3:2:1]oct-3-ylidene]phenylmethyl]benzoyl Chloride Following the protocol of Procedure E and substituting 4-[[8-[2-(4-methoxyphenyl)ethyl]-8-azabicyclo[3:2:1]oct-3-ylidene]phenylmethyl]benzoic acid for 4-[(8-phenethyl-8-azabicyclo[3.2.1]oct-3-ylidene)phenylmethyl]benzoic acid, the title compound was obtained.

EXAMPLE 53

N,N-Diethyl-4-[[8-[2-(4-methoxyphenyl)ethyl]-8-azabicyclo[3:2:1]oct-3-ylidene]phenylmethyl]benzamide Following the protocol of Procedure F and substituting 4-[[8-[2-(4-methoxyphenyl)ethyl]-8-azabicyclo[3:2:1]oct-3-ylidene]phenylmethyl]benzoyl chloride for 4-[(8-phenethyl-8-azabicyclo[3.2.1]oct-3-ylidene)phenylmethyl]benzoyl chloride, the title compound was obtained. MS m/z (MH$^+$) 509.

EXAMPLES 54–63

N,N-Di-R$^2$,R$^3$-4-[[8-[2-(4-methoxyphenyl)ethyl]-8-azabicyclo[3:2:1]oct-3-ylidene]phenylmethyl]benzamides Using the method of Example 26 and substituting the material from Procedure Q for the material from Procedure E, the following compounds were prepared:

| Ex # | Amine | CIMS (MH$^+$) |
|---|---|---|
| 54 | morpholine | 523 |
| 55 | ethylamine | 481 |
| 56 | bis(methoxyethyl)amine | 569 |
| 57 | pyrrolidine | 507 |
| 58 | cis-2,6-dimethylpiperidine | 549 |
| 59 | N-ethyl-(N-methylallyl)amine | 535 |
| 60 | di-n-propylamine | 537 |
| 61 | 2,2,6,6-tetramethylpiperidine | 577 |
| 62 | di-2-propylamine | 537 |

Procedure R

N-Ethyl-4-(4-methoxybenzoyl)benzamide

Following the protocol of Procedure A and substituting 4-(4-methoxybenzoyl)benzoic acid for 4-benzoylbenzoic acid and ethylamine hydrochloride for diethylamine, the title compound was obtained. MS m/z (MH$^+$) 284.

EXAMPLE 63

N-Ethyl4-[(4-methoxyphenyl)-(8-methyl-8-azabicyclo[3:2:1]oct-3-ylidene)methyl]benzamide Following the protocol of Example 1 and substituting N-ethyl-4-(4-methoxybenzoyl)benzamide for N,N-diethyl-4-benzoylbenzamide, the title compound was obtained. MS m/z (MH$^+$) 391.

Procedure S

2,2,2-Trichloroethyl 3-[(ethylcarbamoylphenyl)-(4-methoxyphenyl)methylene]-8-azabicyclo[3:2:1]octanecarboxylate A solution of 1.95 g (5.0 mmol) of N-ethyl-4-[(4-methoxyphenyl)-(8-methyl-8-azabicyclo[3:2:1]oct-3- ylidene)methyl]benzamide, 1.03 mL (7.5 mmol) of 2,2,2-trichloroethyl chloroformate and 0.43 mL (2.5 mmol) of diisopropylethylamine was stirred in 50 mL of benzene and 1.38 g (10 mmol) of $K_2CO_3$ added. The mixture was heated at under reflux for 18 h. Another 0.51 mL of (3.75 mmol) of 2,2,2-trichloroethyl chloroformate and 0.21 mL (1.25 mmol) of diisopropylethylamine was added. The mixture was heated under reflux for 3 h. The reaction was cooled and poured into $H_2O$. The organic layer was washed with dilute HCl and brine, dried ($MgSO_4$) and concentrated to give 2.09 g of a yellow gum. MS m/z ($MH^+$) 553. $^1H$ NMR 300 MHz ($CDCl_3$) δ 7.7 (d, 2H), 7.2 (d, 2H), 7.0 (d, 2H), 6.8 (d, 2H), 6.2 br. s, 1H), 4.9 (d, 1H), 4.7 (d, 1H), 4.3 (br. m, 2H), 3.8 (s, 3H), 3.4 (q, 2H), 2.4 (br. m, 4H), 1.9 (m, 2H), 1.7 (m, 2H), 1.2 (t, 3H).

Procedure T 2,2,2-Trichloroethyl 3-[(ethylcarbamoylphenyl)-(4-hydroxyphenyl)methylene]-8-azabicyclo[3:2:1] octanecarboxylate A solution of 1.03 g (1.82 mmol) of 2,2,2-trichloroethyl 3-[(ethylcarbamoylphenyl)-(4-methoxyphenyl)methylene]-8-azabicyclo[3:2:1]octanecarboxylate in 10 mL of $CHCl_3$ was cooled to –60° C. under $N_2$ and 9.1 mL of 1M $BBr_3$ in $CH_2Cl_2$ was added dropwise. The cooling bath was removed and the mixture stirred at 25° C. for 18 h. Saturated aqueous $NaHCO_3$ was added and the $CH_2CO_2$ was evaporated. The solid (1 g) was collected. $^1H$ NMR 300 MHz ($CDCl_3$) δ 7.8 (d, 2H), 7.2 (d, 2H), 6.9 (d, 2H), 6.7 (d, 2H), 6.2 (br. s, 1H), 4.9 (d, 1H), 4.7 (d, 1H), 4.4 (br. m, 2H), 3.4 (q, 2H), 2.4 (br. m, 4H), 1.9 (m, 2H), 1.7 (m, 2H), 1.2 (t, 3H).

EXAMPLE 64

4-[(8-Azabicyclo[3:2:1]oct-3-ylidene)-(4-hydroxyphenyl)methyl]-N-ethylbenzamide

A 0.73 g sample (11 mmol) of zinc dust was added to a solution of 0.89 g (1.61 mmol) of 2,2,2-trichloroethyl 3-[(ethylcarbamoylphenyl)-(4-hydroxyphenyl)methylene]-8-azabicyclo[3:2:1]octanecarboxylate in 9 mL of glacial HOAc. The mixture was heated under reflux for 5 h then cooled and the solid removed by filtration and washed with HOAc. The solvent was evaporated and $K_2CO_3$ was added. The mixture was extracted six times with 20% EtOH in $CHCl_3$. The solution was dried ($Na_2SO_4$) and concentrated. The residue was crystallized from EtOH/2-PrOH to give 0.24 g of a white solid. MS m/z ($MH^+$) 363. $^1H$ NMR (DMSO-$d_6$) δ 8.5 (t, 1H), 7.8 (d, 2H), 7.2 (d, 2H), 6.9 (d, 2H), 6.7 (d, 2H), 3.3 (br. m, 4H), 2.2 (br. m, 4H), 1.5 (m, 4H), 1.1 (t, 3H).

Procedure U

N-Diethyl-4-(4-methoxybenzoyl)benzamide

A mixture of 0.75 g (5.5 mmol) of 4-methoxybenzeneboronic acid, 1.5 g (5 mmol) N,N-diethyl-4-iodobenzamide, 0.1 g (0.15 mmol) bistriphenylphosphine palladium(II)dichloride and 2.07 g (15 mmol) of $K_2CO_3$ in 30 mL of anisole was flushed with carbon monoxide then heated at 80° C. under a CO atmosphere for 5 h. The mixture was filtered and the solvent evaporated. The residue was flash chromatographed 20% acetone in hexane to give the title compound. MS m/z ($MH^+$) 312.

EXAMPLE 65

N,N-Diethyl-4-[(4-methoxyphenyl)-(8-methyl-8-azabicyclo[3:2:1]oct-3-ylidene)methyl]benzamide Following the protocol of Example 1 and substituting N,N-diethyl-4-(4-methoxybenzoyl)benzamide for N,N-diethyl-4-benzoylbenzamide, the title compound was obtained. MS m/z ($MH^+$) 419.

Procedure V 2,2,2-Trichloroethyl 3-[(diethylcarbamoylphenyl)-(4-methoxyphenyl)methylene]-8-azabicyclo[3:2:1] octanecarboxylate Following the protocol of Procedure S and substituting N,N-diethyl-4-[(4-methoxyphenyl)-(8-methyl-8-azabicyclo[3:2:1]oct-3-ylidene)methyl]benzamide for N-ethyl-4-[(4-methoxyphenyl)-(8-methyl-8-azabicyclo[3:2:1]oct-3-ylidene)methyl]benzamide, the title compound was obtained.

Procedure W 2,2,2-Trichloroethyl 3-[(diethylcarbamoylphenyl)-(4-hydroxyphenyl)methylene]-8-azabicyclo[3:2:1] octanecarboxylate Following the protocol of Procedure T and substituting 2,2,2-trichloroethyl 3-[(diethylcarbamoylphenyl)-(4-methoxyphenyl)methylene]-8-azabicyclo[3:2:1] octanecarboxylate for 2,2,2-trichloroethyl 3-[(ethylcarbamoylphenyl)-(4-methoxyphenyl)methylene]-8-azabicyclo[3:2:1]octanecarboxylate, the title compound was obtained.

EXAMPLE 66

4-[(8-Azabicyclo[3:2:1]oct-3-ylidene)-(4-hydroxyphenyl)methyl]-N-diethylbenzamide Following the protocol for Example 64 and substituting 2,2,2-trichloroethyl 3-[(diethylcarbamoylphenyl)-(4-hydroxyphenyl)methylene]-8-azabicyclo[3:2:1] octanecarboxylate for 2,2,2-trichloroethyl 3-[(ethylcarbamoylphenyl)-(4-hydroxyphenyl)methylene]-8-azabicyclo[3:2:1]octanecarboxylate, the title compound was obtained. MS m/z ($MH^+$) 391.

EXAMPLE 67

N,N-Diethyl-4-[(4-methoxyphenyl)-[8-[2-(4-methoxyphenyl)ethyl]-8-azabicyclo[3:2:1]oct-3-ylidene]methyl]benzamide Following the protocol of Example 1 and substituting 8-[2-(4-methoxyphenyl)ethyl]-8-azabicyclo[3:2:1]octanone for tropinone, the title compound was obtained. MS m/z ($MH^+$) 539.

EXAMPLE 68

N,N-Diethyl-4-[(4-hydroxyphenyl)-[8-[2-(4-hydroxyphenyl)ethyl]-8-azabicyclo[3:2:1]oct-3-ylidene]methyl]benzamide Following the protocol of Example 64 and substituting N,N-diethyl-4-[(4-methoxyphenyl)-[8-[2-(4-methoxyphenyl)ethyl]-8-azabicyclo[3:2:1]oct-3-ylidene] methyl]benzamide for 2,2,2-trichloroethyl 3-[(ethylcarbamoylphenyl)-(4-hydroxyphenyl)methylene]-8-azabicyclo[3:2:1]octanecarboxylate, the title compound was obtained. MS m/z ($MH^+$) 511.

EXAMPLE 69

N-Ethyl-4-[[8-[2-(4-hydroxyphenyl)ethyl]-8-azabicyclo[3:2:1]oct-3-ylidene]phenylmethyl] benzamide Following the protocol of Procedure T and substituting N-ethyl-4-[[8-[2-(4-methoxyphenyl)ethyl]-8-azabicyclo

[3:2:1]oct-3-ylidene]phenylmethyl] benzamide for 2,2,2-trichloroethyl 3-[(ethylcarbamoylphenyl)-(4-methoxyphenyl)methylene]-8-azabicyclo[3:2:1]octanecarboxylate, the title compound was obtained. MS m/z (MH$^+$) 467.

EXAMPLE 70

N,N-Diethyl-4-[[8-[2-(4-hydroxyphenyl)ethyl]-8-azabicyclo[3:2:1]oct-3-ylidene]phenylmethyl]benzamide Following the protocol of Procedure T and substituting N,N-diethyl-4-[[8-[2-(4-methoxyphenyl)ethyl]-8-azabicyclo[3:2:1]oct-3-ylidene]phenylmethyl]benzamide for 2,2,2-trichloroethyl 3-[(ethylcarbamoylphenyl)-(4-methoxyphenyl)methylene]-8-azabicyclo[3:2:1]octanecarboxylate, the title compound was obtained. MS m/z (MH$^+$) 495.

BIOLOGICAL EXAMPLES

Screening Assay for δ-Opioid and μ-Opioid Receptor Binding Rat Brain δ-Opioid Receptor Binding Assay The activity of the compounds of the invention as analgesics was demonstrated by the rat brain δ-opioid receptor binding assay as described below.

Procedure

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% Inhibition was calculated as follows:

$$1 - \left(\frac{\text{(test compound } dpm - \text{nonspecific } dpm)}{\text{(total } dpm - \text{nonspecific } dpm)}\right) \times 100\%$$

$K_i$ value is calculated using the LIGAND (Munson, P. J. and Rodbard, D., Anal. Biochem. 107: 220–239, 1980) data analysis program.

Table 3 shows the biological activity (in $K_i$ value) for 10 nM solutions of the present compounds as measured in the rat brain δ-opioid receptor binding assay.

TABLE 3

| Example # | δ $K_i$ (nM) | Example # | δ $K_i$ (nM) | Example # | δ $K_i$ (nM) |
|---|---|---|---|---|---|
| 1 | 1.2 | 25 | 9.9 | 48 | 48.2 |
| 2 | 0.1 | 26 | 7.5 | 49 | 4.96 |
| 3 | 0.023 | 27 | 46.7 | 50 | 8.5 |
| 4 | 0.36 | 28 | 4.7 | 51 | 5.7 |
| 5 | 0.06 | 29 | 35.9 | 52 | 0.75 |
| 6 | 0.025 | 30 | 35.2 | 53 | 2.9 |
| 7 | 2.6 | 31 | 49 | 54 | 57 |
| 8 | 13 | 32 | 16.6 | 55 | 225 |
| 9 | 3.5 | 33 | 24 | 56 | 24 |
| 10 | 1.4 | 34 | 11 | 57 | 15 |
| 11 | 0.38 | 35 | 2.9 | 58 | 18 |
| 12 | 18.5 | 36 | 7.4 | 59 | 3.9 |
| 13 | 6.3 | 37 | 352 | 60 | 12 |
| 14 | 1.1 | 38 | 32 | 61 | 15.5 |
| 15 | 6.8 | 39 | 49 | 62 | 30.7 |
| 17 | 0.23 | 40 | 102 | 64 | 4.5 |
| 18 | 0.39 | 41 | 331 | 66 | 0.58 |
| 19 | 0.7 | 42 | 924 | 67 | 24.7 |
| 20 | 0.01 | 43 | 1520 | 68 | 0.41 |
| 21 | 0.56 | 44 | 178 | 69 | 1.08 |
| 22 | 92 | 45 | 19.8 | 70 | 0.7 |
| 23 | 0.23 | 46 | 404 | | |
| 24 | 42.1 | 47 | 3.2 | | |

Rat Brain μ-Opioid Receptor Binding Assay

The activity of compounds of the invention as analgesics is demonstrated by the rat brain μ-opioid receptor binding assay as described below.

Procedure

Male, Wistar rats (150–250 g, VAF, Charles River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the μ-opioid binding assays. Following incubation with the m-selective peptide ligand [$^3$H] DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% Inhibition is calculated as follows:

$$1 - \left(\frac{\text{(test compound } dpm - \text{nonspecific } dpm)}{\text{(total } dpm - \text{nonspecific } dpm)}\right) \times 100\%$$

$K_i$ value is calculated using the LIGAND (Munson, P. J. and Rodbard, D., Anal. Biochem. 107: 220–239, 1980) data analysis program.

Mouse Acetylcholine Bromide-Induced Abdominal Constriction Assay

The activity of compounds of the invention as analgesics was further demonstrated by the mouse acetylcholine bromide-induced abdominal constriction assay as described below.

Procedure

The mouse acetylcholine-induced abdominal constriction assay (as described by Collier et al. in *Brit. J. Pharmacol. Chem. Ther.,* 1968, 32: 295–310 with minor modifications) was used to assess analgesic potency of the compounds of formula (I). The test drugs or appropriate vehicles were administered orally (p.o.) and 30 min later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten min observation period for the occurrence of an abdominal constriction response (defined as a wave of constriction and elongation passing caudally along the abdominal wall, accompanied by a twisting of the trunk and followed by extension of the hind limbs). For compounds of the present invention, the percent inhibition of this response to a nociceptive stimulus (equated to % analgesia) was calculated as follows:

$$\% \text{ Inhibition of response (i.e., } \% \text{ analgesia)} = \frac{(\text{No. of control animal responses} - \text{No. of drug-treated animal responses})}{(\text{No. of control animals responding})} \times 100$$

As a result of the mouse acetylcholine bromide-induced abdominal constriction assay, the compound of Example 1 measured an 87% inhibition response at a dose of 150 μmole/Kg p.o.

What is claimed is:

1. A compound of Formula (I):

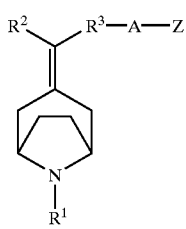

wherein:

$R^1$ is selected from the group consisting of hydrogen, $C_{1-8}$alkyl, $halo_{1-3}$ ($C_{1-8}$) alkyl, $C_{2-8}$alkenyl, $C_{1-8}$alkoxy ($C_{2-8}$) alkenyl, $C_{2-8}$alkynyl, $C_{1-8}$alkoxy ($C_{2-8}$) alkynyl, cycloalkyl, cycloalkyl ($C_{1-8}$) alkyl, cycloalkylcarbonyl ($C_{1-8}$) alkyl, cycloalkyl ($C_{2-8}$) alkenyl, cycloalkyl ($C_{2-8}$) alkynyl, heterocyclyl, heterocyclyl ($C_{1-8}$) alkyl, heterocyclylcarbonyl ($C_{1-8}$) alkyl, heterocyclyl ($C_{2-8}$) alkenyl, heterocyclyl ($C_{2-8}$)alkynyl, aryl, aryl ($C_{1-8}$) alkyl, arylcarbonyl ($C_{1-8}$)alkyl, aryl ($C_{2-8}$)alkenyl, aryl ($C_{2-8}$)alkynyl, arylaminocarbonyl ($C_{1-8}$) alkyl, heteroaryl ($C_{1-8}$) alkyl, heteroarylcarbonyl ($C_{1-8}$) alkyl, heteroaryl ($C_{2-8}$) alkenyl, heteroaryl ($C_{2-8}$) alkynyl, heteroarylaminocarbonyl ($C_{1-8}$) alkyl, $(R^{1a})_2$—N—($C_{1-8}$) alkyl, $R^{1a}$—O—($C_{1-8}$) alkyl, $R^{1a}$—S—($C_{1-8}$) alkyl, $R^{1a}$—SO—($C_{1-8}$) alkyl and $R^{1a}$—SO$_2$—($C_{1-8}$) alkyl; wherein heterocyclyl is optionally substituted with one to three substituents independently selected from the group consisting of $C_{1-6}$alkyl, $C_{2-6}$alkenyl, $C_{1-6}$alkoxy, amino, $C_{1-6}$alkylamino, di ($C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, oxo, cyano, trifluoromethyl and trifluoromethoxy; and, wherein aryl and heteroaryl are optionally substituted with one to three substituents independently selected from the group consisting of $C_{1-6}$alkyl, $C_{2-6}$alkenyl, $C_{1-6}$alkoxy, amino, $C_{1-6}$alkylamino, di ($C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy;

$R^{1a}$ is independently selected from the group consisting of hydrogen, $C_{1-8}$alkyl, $C_{1-8}$alkoxy($C_{1-8}$) alkyl, hydroxy ($C_{1-8}$) alkyl, $halo_{1-3}$($C_{1-8}$)alkyl, $halo_{1-3}$($C_{1-8}$)alkoxy ($C_{1-8}$)alkyl, $C_{2-8}$alkenyl, $C_{2-8}$alkynyl, cycloalkyl, cycloalkyl ($C_{1-8}$) alkyl, heterocyclyl, heterocyclyl ($C_{1-8}$) alkyl, heterocyclyl ($C_{1-8}$) alkenyl, heterocyclyl ($C_{1-8}$) alkynyl, aryl, aryl ($C_{1-8}$) alkyl, aryl ($C_{1-8}$) alkenyl, aryl ($C_{1-8}$)alkynyl, arylcarbonyl ($C_{1-8}$)alkyl, heteroaryl, heteroaryl ($C_{1-8}$) alkyl, heteroaryl ($C_{1-8}$) alkenyl, heteroaryl ($C_{1-8}$) alkynyl and heteroarylcarbonyl ($C_{1-8}$) alkyl; wherein heterocyclyl is optionally substituted with one to three substituents independently selected from the group consisting of $C_{1-6}$alkyl, $C_{2-6}$alkenyl, $C_{1-6}$alkoxy, amino, $C_{1-6}$alkylamino, di ($C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, oxo, cyano, trifluoromethyl and trifluoromethoxy; and, wherein aryl and heteroaryl are optionally substituted with one to three substituents independently selected from the group consisting of $C_{1-6}$alkyl, $C_{2-6}$alkenyl, $C_{1-6}$alkoxy, amino, $C_{1-6}$alkylamino, di ($C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy;

$R^2$ is selected from the group consisting of aryl and heteroaryl optionally substituted with one to three substituents independently selected from the group consisting of $C_{1-6}$alkyl, $C_{2-6}$alkenyl, $C_{1-6}$alkoxy, amino, $C_{1-6}$alkylamino, di ($C_{1-6}$alkyl) amino, $C_{1-6}$alkylcarbonyl, $C_{1-6}$alkylcarbonyloxy, $C_{1-6}$alkyloxycarbonyl, $C_{1-6}$alkylaminocarbonyl, $C_{1-6}$alkylcarbonylamino, $C_{1-6}$alkylthio, $C_{1-6}$alkylsulfonyl, halogen, hydroxy, cyano, trifluoromethyl and trifluoromethoxy; alternatively, when aryl and heteroaryl are substituted with two substituents attached to adjacent carbon atoms, the two substituents can together form a single fused moiety; wherein the moiety is selected from the group consisting of —(CH$_2$)$_{3-5}$— and —O(CH$_2$)$_{1-3}$O—;

$R^3$ is selected from the group consisting of aryl and heteroaryl optionally substituted with one or two substituents in addition to the -A-Z moiety independently selected from the group consisting of $C_{1-6}$alkyl, $C_{2-6}$alkenyl, $C_{1-6}$alkoxy, amino, $C_{1-6}$alkylamino, di ($C_{1-6}$alkyl)amino, $C_{1-6}$alkylcarbonyl, $C_{1-6}$alkylcarbonyloxy, $C_{1-6}$alkyloxycarbonyl, $C_{1-6}$alkylaminocarbonyl, $C_{1-6}$alkylcarbonylamino, $C_{1-6}$alkylthio, $C_{1-6}$alkylsulfonyl, halogen, hydroxy, cyano, trifluoromethyl and trifluoromethoxy; alternatively, when aryl and heteroaryl are substituted with two optional substituents attached to adjacent carbon atoms, the two substituents can together form a single fused moiety; wherein the moiety is selected from the group consisting of —(CH$_2$)$_{3-5}$— and —O(CH$_2$)$_{1-3}$O—;

A is selected from the group consisting of —C(=X)— and —SO$_2$—;

X is selected from the group consisting of O and S;

Z is selected from the group consisting of —O($R^4$) and —N($R^5$)($R^6$);

$R^4$ is selected from the group consisting of hydrogen, $C_{1-8}$alkyl (optionally substituted with one to three halogen substituents), $C_{1-8}$alkoxy($C_{1-8}$)alkyl, $C_{2-8}$alkenyl, cycloalkyl, cycloalkyl ($C_{1-8}$)alkyl, heterocyclyl, heterocyclyl ($C_{1-8}$) alkyl, aryl, aryl ($C_{1-8}$)alkyl, heteroaryl, heteroaryl ($C_{1-8}$) alkyl, amino ($C_{1-8}$) alkyl, $C_{1-8}$alkylamino ($C_{1-8}$) alkyl, di ($C_{1-8}$) alkylamino($C_{1-6}$)alkyl and hydroxy($C_{1-8}$)alkyl; wherein heterocyclyl is optionally substituted with one to three substituents independently selected from the group consisting of $C_{1-6}$alkyl, $C_{1-6}$alkoxy, $C_{2-6}$alkenyl, cycloalkyl, trifluoromethyl, halogen, hydroxy, oxo and cyano; and, wherein aryl is optionally substituted with one to four substituents independently selected from the group consisting of $C_{1-6}$alkyl, $C_{1-6}$alkoxy, $C_{2-6}$alkenyl, cycloalkyl, —OCH$_2$O—, —O(CH$_2$)$_2$O—, trifluoromethyl, halogen, hydroxy and cyano;

$R^5$ and $R^6$ are independently selected from the group consisting of hydrogen, $C_{1-8}$alkyl (optionally substituted with one to three halogen substituents), $C_{1-8}$alkoxy($C_{1-8}$) alkyl, $C_{2-8}$alkenyl, cycloalkyl, cycloalkyl ($C_{1-8}$) alkyl, heterocyclyl, heterocyclyl ($C_{1-8}$)alkyl, aryl, aryl ($C_{1-8}$)alkyl, heteroaryl, heteroaryl ($C_{1-8}$) alkyl, amino ($C_{1-8}$) alkyl, $C_{1-8}$alkylamino($C_{1-8}$) alkyl, di ($C_{1-8}$)alkylamino($C_{1-8}$)alkyl, aminoimino, aminocarbonyl, aminocarbonyl ($C_{1-8}$) alkyl, aryloxycarbonyl, aryloxycarbonylamino ($C_{1-8}$) alkyl, heteroaryloxycarbonylamino ($C_{1-8}$) alkyl, hydroxy($C_{1-8}$) alkyl and trifluoro ($C_{1-4}$)alkoxy; wherein heterocyclyl is optionally substituted with one to three substituents independently selected from the group consisting of $C_{1-6}$alkyl, $C_{1-6}$alkoxy, $C_{2-6}$alkenyl, cycloalkyl, trifluoromethyl, halogen, hydroxy, oxo and cyano; and, wherein aryl is optionally substituted with one to four substituents independently selected from the group consisting of $C_{1-6}$alkyl, $C_{1-6}$alkoxy, $C_{2-6}$alkenyl, cycloalkyl, —OCH$_2$O—, —O(CH$_2$)$_2$O—, trifluoromethyl, halogen, hydroxy and cyano; alternatively, $R^5$ and $R^6$ may, together with the nitrogen to which they are attached, form a fused heterocyclyl moiety optionally substituted with one to four substituents independently selected from the group consisting of $C_{1-6}$alkyl, $C_{1-6}$alkoxy, $C_{2-6}$alkenyl, cycloalkyl, trifluoromethyl, halogen, hydroxy and cyano;

wherein the cycloalkyl in any cycloalkyl containing substituent is a branched or unbranched cyclic aliphatic hydrocarbon chain of three to seven carbon atom members;

wherein the heteroaryl in any heteroaryl containing substituent is an aromatic ring of five or six members wherein the ring has at least one heteroatom member selected from the group consisting of nitrogen, oxygen and sulfur, and wherein said five-membered ring optionally contains up to two additional nitrogens, and wherein said six-membered ring optionally contains from one to three additional nitrogen atoms wherein at most two nitrogen atoms are adjacent;

wherein the heterocyclyl in any heterocyclyl containing substituent is a nonaromatic ring of five to seven members in which one to four members are nitrogen or a nonaromatic ring of five to seven members in which zero, one or two members are nitrogen and one member is oxygen or sulfur, wherein the heterocyclyl optionally contains zero, one or two unsaturated bonds, and wherein optionally up to three carbon members of the hetercyclyl adjacent to nitrogen members is oxo substituted, and wherein optionally, the heterocyclyl ring is fused to a ring selected from the group consisting of a benzene ring, a 5 or 6 membered heteroaryl containing one of O, S or N wherein said heteroaryl optionally contains one additional nitrogen, a 5 to 7 membered alicyclic ring, and a 5 to 7 membered heterocyclyl ring of the same definition as above but absent the option of a further fused ring; and wherein the alkylthio of any alkylthio containing substituent is attached to the rest of the molecule through its sulfur atom;

or enantiomers, diastereomers or pharmaceutically acceptable salts thereof.

2. The compound of claim 1 wherein $R^1$ is selected from the group consisting of hydrogen, $C_{1-8}$alkyl, $C_{2-8}$alkenyl, $C_{2-8}$alkynyl, cycloalkyl, cycloalkyl($C_{1-8}$)alkyl, heterocyclyl, heterocyclyl($C_{1-8}$)alkyl, heterocyclylcarbonyl($C_{1-8}$)alkyl, aryl($C_{1-8}$)alkyl, arylcarbonyl($C_{1-8}$)alkyl, aryl($C_{2-8}$)alkynyl, arylaminocarbonyl($C_{1-8}$)alkyl, heteroaryl($C_{1-8}$)alkyl, ($R^{1a}$)$_2$—N—($C_{1-8}$)alkyl and $R^{1a}$—O—($C_{1-8}$)alkyl; wherein heterocyclyl is optionally substituted with one to three substituents independently selected from the group consisting of $C_{1-6}$alkyl, $C_{1-6}$alkoxy, halogen, hydroxy, oxo and cyano; and, wherein aryl is optionally substituted with one to three substituents independently selected from the group consisting of $C_{1-6}$alkyl, $C_{1-6}$alkoxy, halogen, hydroxy and cyano.

3. The compound of claim 1 wherein $R^1$ is selected from the group consisting of hydrogen, methyl, ethyl, n-propyl, i-propyl, n-butyl, t-butyl, n-hexyl, butenyl, allyl, 3,3-dimethallyl, cyclopropyl, cyclopropyl($C_{1-3}$)alkyl, cyclohexyl, cyclohexyl($C_{1-3}$)alkyl, pyrrolidinyl, pyrrolidinyl($C_{1-3}$)alkyl, 1,3-dioxolanyl($C_{1-3}$)alkyl, 2-imidazolinyl, 2-imidazolinyl($C_{1-3}$)alkyl, imidazolidinyl, imidazolidinyl($C_{1-3}$)alkyl, 2-pyrazolinyl, 2-pyrazolinyl ($C_{1-3}$)alkyl, pyrazolidinyl, pyrazolidinyl($C_{1-3}$)alkyl, piperidinyl, piperidinyl($C_{1-3}$)alkyl, morpholinyl, morpholinyl($C_{1-3}$)alkyl, thiomorpholinyl, thiomorpholinyl ($C_{1-3}$)alkyl, piperazinyl, piperazinyl($C_{1-3}$)alkyl, [4-($C_{1-3}$) alkyl-5-oxo-1,4-dihydrotetrazol-1-yl]($C_{1-3}$)alkyl, piperonyl, (1,3-benzodioxol-5-yl)($C_{2-3}$)alkyl, (2,3-dihydro-1,4-benzodioxin-6-yl)carbonyl($C_{1-3}$)alkyl, (3,4-dihydro-2H-1, 5-benzodioxepin-7-yl)carbonyl($C_{1-3}$)alkyl, benzyl, phenyl ($C_{2-3}$)alkyl, phenyl($C_{2-3}$)alkynyl, diphenyl($C_{1-3}$)alkyl, phenylcarbonyl($C_{1-3}$)alkyl, phenylaminocarbonyl($C_{1-3}$) alkyl, furyl($C_{1-3}$)alkyl, thienyl($C_{1-3}$)alkyl, pyrrolyl($C_{1-3}$) alkyl, oxazolyl($C_{1-3}$)alkyl, thiazolyl($C_{1-3}$)alkyl, imidazolyl ($C_{1-3}$)alkyl, pyrazolyl($C_{1-3}$)alkyl, isoxazolyl($C_{1-3}$)alkyl, isothiazolyl($C_{1-3}$)alkyl, 1,2,3-oxadiazolyl($C_{1-3}$)alkyl, 1,2,3-triazolyl($C_{1-3}$)alkyl, 1,3,4-thiadiazolyl($C_{1-3}$)alkyl, pyridinyl ($C_{1-3}$)alkyl, pyridazinyl($C_{1-3}$)alkyl, pyrimidinyl($C_{1-3}$)alkyl, pyrazinyl($C_{1-3}$)alkyl, 1,3,5-triazinyl($C_{1-3}$)alkyl, indolyl ($C_{1-3}$)alkyl, benzo[b]furyl($C_{1-3}$)alkyl, benzo[b]thienyl($C_{1-3}$) alkyl, ($R^{1a}$)$_2$—N—($C_{1-3}$)alkyl and $R^{1a}$—O—($C_{1-3}$)alkyl; wherein pyrrolidinyl, 2-imidazolinyl, imidazolidinyl, 2-pyrazolinyl, pyrazolidinyl, piperidinyl, morpholinyl, thiomorpholinyl and piperazinyl are optionally substituted with one to three substituents selected from oxo; and, wherein phenyl is optionally substituted with one to three substituents independently selected from the group consisting of methyl, ethyl, n-propyl, n-butyl, methoxy, ethoxy, propoxy, butoxy, chlorine, fluorine, hydroxy and cyano.

4. The compound of claim 1 wherein $R^1$ is selected from the group consisting of hydrogen, methyl, n-propyl, n-butyl, allyl, 3,3-dimethallyl, cyclopropylmethyl, cyclohexylethyl, 2-(4-ethyl-5-oxo-1,4-dihydrotetrazol-1-yl)ethyl, piperonyl, 2-(1,3-benzodioxol-5-yl)ethyl, 2-(2,3-dihydro-1,4-benzodioxin-6-yl)-2-oxoethyl, 2-(3,4-dihydro-2H-1,5-benzodioxepin-7-yl)-2-oxoethyl, benzyl, phenethyl, phenylpropyl, phenoxyethyl, phenylcarbonylmethyl, phenylcarbonylethyl, phenylaminocarbonylmethyl, thienylmethyl, thienylethyl, imidazolylmethyl, pyridinylmethyl and indolylethyl; wherein phenyl is optionally substituted with one to three substituents independently selected from the group consisting of methoxy, fluorine, hydroxy and cyano.

5. The compound of claim 1 wherein $R^{1a}$ is independently selected from the group consisting of hydrogen, $C_{1-8}$alkyl and aryl; wherein aryl is optionally substituted with one to three substituents independently selected from the group consisting of $C_{1-6}$alkyl, $C_{2-6}$alkenyl, $C_{1-6}$alkoxy, amino, $C_{1-6}$alkylamino, di($C_{1-6}$alkyl)amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy.

6. The compound of claim 1 wherein $R^{1a}$ is independently selected from the group consisting of hydrogen, methyl, ethyl, n-propyl, i-propyl, n-butyl, t-butyl and phenyl; wherein phenyl is optionally substituted with one to three substituents independently selected from the group consisting of $C_{1-6}$alkyl, $C_{1-6}$alkoxy, di($C_{1-6}$alkyl)amino, halogen, trifluoromethyl and trifluoromethoxy.

7. The compound of claim 1 wherein $R^{1a}$ is independently selected from the group consisting of methyl, ethyl and phenyl.

8. The compound of claim 1 wherein $R^2$ is selected from the group consisting of phenyl, naphthalenyl, furyl, thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridinyl, pyridazinyl, pyrimidinyl, pyrazinyl, 1,3,5-triazinyl, indolyl, benzo[b]furyl and benzo[b]thienyl optionally substituted with one to three substituents independently selected from the group consisting of $C_{1-3}$alkyl, $C_{2-3}$alkenyl, $C_{1-3}$alkoxy, amino, $C_{1-3}$alkylamino, di($C_{1-3}$alkyl)amino, $C_{1-3}$alkylcarbonyl, $C_{1-3}$alkylcarbonyloxy, $C_{1-3}$alkylcarbonylamino, chlorine, fluorine, hydroxy, trifluoromethyl and trifluoromethoxy.

9. The compound of claim 1 wherein $R^2$ is selected from the group consisting of phenyl, furyl, thienyl, pyridinyl and benzo[b]furyl optionally substituted with one substituent selected from the group consisting of methyl, ethyl, methoxy, ethoxy, methylamino, ethylamino, dimethylamino, diethylamino, methylcarbonyl, methylcarbonyloxy, methylcarbonylamino, fluorine, hydroxy, trifluoromethyl and trifluoromethoxy.

10. The compound of claim 1 wherein $R^2$ is selected from phenyl optionally substituted with one substituent selected from the group consisting of methoxy and hydroxy.

11. The compound of claim 1 wherein $R^3$ is selected from the group consisting of phenyl, naphthalenyl, furyl, thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridinyl, pyridazinyl, pyrimidinyl, pyrazinyl, 1,3,5-triazinyl, indolyl, benzo[b]furyl and benzo[b]thienyl optionally substituted with one or two substituents in addition to the -A-Z moiety independently selected from the group consisting of methyl, ethyl, n-propyl, i-propyl, allyl, methoxy, ethoxy, amino, $C_{1-3}$alkylamino, di($C_{1-3}$)alkylamino, $C_{1-3}$alkylcarbonyl, $C_{1-3}$alkylcarbonyloxy, $C_{1-3}$alkylcarbonyl, $C_{1-3}$alkylaminocarbonyl, $C_{1-3}$alkylcarbonylamino, $C_{1-3}$alkylthio, $C_{1-3}$alkylsulfonyl, chloro, fluoro, hydroxy, cyano, trifluoromethyl and trifluoromethoxy; alternatively, when phenyl is substituted with two optional substituents attached to adjacent carbon atoms, the two substituents can together form a single fused moiety; wherein the moiety is selected from the group consisting of —(CH$_2$)$_{3-5}$— and —O(CH$_2$)$_{1-3}$O—.

12. The compound of claim 1 wherein $R^3$ is phenyl substituted with the moiety -A-Z at the 3 or 4 position.

13. The compound of claim 1 wherein A is —C(=X)—.

14. The compound of claim 1 wherein Z is —N($R^5$)($R^6$).

15. The compound of claim 1 wherein $R^4$ is selected from the group consisting of $C_{1-8}$alkyl (optionally substituted with one to three halogen substituents), $C_{2-8}$alkenyl, aryl and aryl($C_{1-8}$)alkyl; wherein aryl is optionally substituted with one to two substituents independently selected from the group consisting of $C_{1-8}$alkyl, —OCH$_2$O—, —O(CH$_2$)$_2$O— and halogen.

16. The compound of claim 1 wherein $R^4$ is selected from the group consisting of $C_{1-3}$alkyl (optionally substituted with one or three fluorine substituents), $C_{2-4}$alkenyl, phenyl and benzyl; wherein phenyl is optionally substituted with one to two substituents independently selected from the group consisting of $C_{1-3}$alkyl, —OCH$_2$O—, —O(CH$_2$)$_2$O— and fluorine.

17. The compound of claim 1 wherein $R^4$ is selected from the group consisting of methyl, ethyl, 3-methallyl, phenyl and benzyl; wherein phenyl is optionally substituted with one substituent selected from the group consisting of methyl and fluorine.

18. The compound of claim 1 wherein $R^5$ and $R^6$ are independently selected from the group consisting of hydrogen, $C_{1-4}$alkyl, fluoro($C_{1-3}$)alkyl, trifluoro($C_{1-3}$)alkyl, $C_{1-3}$alkoxy($C_{1-3}$)alkyl, $C_{2-5}$alkenyl, cyclopropyl, cyclopropyl($C_{1-3}$)alkyl, cyclopentyl, cyclopentyl($C_{1-3}$)alkyl, cyclohexyl, cyclohexyl($C_{1-3}$)alkyl, pyrrolidinyl, pyrrolidinyl($C_{1-3}$)alkyl, 1,3-dioxolanyl, 1,3-dioxolanyl($C_{1-3}$)alkyl, 2-imidazolinyl, 2-imidazolinyl($C_{1-3}$)alkyl, imidazolidinyl, imidazolidinyl($C_{1-3}$)alkyl, 2-pyrazolinyl, 2-pyrazolinyl($C_{1-3}$)alkyl, pyrazolidinyl($C_{1-3}$)alkyl, piperidinyl, piperidinyl($C_{1-3}$)alkyl, morpholinyl, morpholinyl($C_{1-3}$)alkyl, thiomorpholinyl, thiomorpholinyl($C_{1-3}$)alkyl, piperazinyl, piperazinyl($C_{1-3}$)alkyl, piperonyl, phenyl, benzyl, phenyl($C_{2-3}$)alkyl, furyl, furyl($C_{1-3}$)alkyl, thienyl, thienyl($C_{1-3}$)alkyl, pyrrolyl($C_{1-3}$)alkyl, oxazolyl, oxazolyl($C_{1-3}$)alkyl, thiazolyl, thiazolyl($C_{1-3}$)alkyl, imidazolyl, imidazolyl($C_{1-3}$)alkyl, pyrazolyl, pyrazolyl ($C_{1-3}$)alkyl, isoxazolyl, isoxazolyl($C_{1-3}$)alkyl, isothiazolyl, isothiazolyl($C_{1-3}$)alkyl, 1,2,3-oxadiazolyl, 1,2,3-oxadiazolyl ($C_{1-3}$)alkyl, 1,2,3-triazolyl, 1,2,3-triazolyl($C_{1-3}$)alkyl, 1,3,4-thiadiazolyl, 1,3,4-thiadiazolyl($C_{1-3}$)alkyl, pyridinyl, pyridinyl($C_{1-3}$)alkyl, pyridazinyl, pyridazinyl($C_{1-3}$)alkyl, pyrimidinyl, pyrimidinyl($C_{1-3}$)alkyl, pyrazinyl, pyrazinyl ($C_{1-3}$)alkyl, 1,3,5-triazinyl, 1,3,5-triazinyl($C_{1-3}$)alkyl, indolyl($C_{1-3}$)alkyl, benzo[b]furyl, benzo[b]furyl($C_{1-3}$)alkyl, benzo[b]thienyl, benzo[b]thienyl($C_{1-3}$)alkyl, benzimidazolyl, benzimidazolyl($C_{1-3}$)alkyl, amino($C_{1-3}$) alkyl, $C_{1-3}$alkylamino($C_{1-3}$)alkyl, di($C_{1-3}$)alkylamino($C_{1-3}$) alkyl, aminoimino, hydroxy($C_{1-3}$)alkyl and trifluoro($C_{1-4}$) alkoxy; wherein pyrrolidinyl, 1,3-dioxolanyl, 2-imidazolinyl, imidazolidinyl, 2-pyrazolinyl, pyrazolidinyl, piperidinyl, morpholinyl, thiomorpholinyl, piperazinyl are optionally substituted with one to three substituents independently selected from the group consisting of $C_{1-4}$alkyl and oxo; and, wherein phenyl is optionally substituted with one to four substituents independently selected from the group consisting of $C_{1-4}$alkyl, C, alkoxy, —OCH$_2$O—, —O(CH$_2$)$_2$O—, halogen, hydroxy and cyano;

alternatively, $R^5$ and $R^6$ may, together with the nitrogen to which they are attached, form a fused heterocyclyl moiety selected from the group consisting of pyrrolidinyl, imidazolidinyl, pyrazolidinyl, piperidinyl, morpholinyl, thiomorpholinyl and piperazinyl optionally substituted with one to four substituents independently selected from $C_{1-4}$alkyl.

19. The compound of claim 1 wherein $R^5$ and $R^6$ are independently selected from the group consisting of hydrogen, methyl, ethyl, n-propyl, i-propyl, t-butyl, fluoro$(C_{1-3})$alkyl, methoxy$(C_{1-3})$alkyl, methallyl, cyclopropyl, cyclohexyl, phenyl, thiazolyl, imidazolyl$(C_{1-3})$alkyl, benzimidazolyl$(C_{1-3})$alkyl, dimethylamino$(C_{1-3})$alkyl and hydroxy$(C_{1-3})$alkyl; wherein phenyl is optionally substituted with one to three substituents selected from fluorine; alternatively, $R^5$ and $R^6$ may, together with the nitrogen to which they are attached, form a fused heterocyclyl moiety selected from the group consisting of pyrrolidinyl, piperidinyl and morpholinyl optionally substituted with one to four substituents independently selected from the group consisting of methyl, ethyl, n-propyl and n-butyl.

20. The compound of claim 1 wherein $R^5$ and $R^6$ are independently selected from the group consisting of hydrogen, methyl, ethyl, n-propyl, i-propyl, t-butyl, 2-fluoroethyl, methoxyethyl, methallyl, cyclopropyl, cyclohexyl, phenyl, thiazolyl, 2-(2-imidazolyl)ethyl, benzimidazolylmethyl, dimethylaminopropyl and hydroxyethyl; wherein phenyl is optionally substituted with fluorine; alternatively, $R^5$ and $R^6$ may, together with the nitrogen to which they are attached, form a fused heterocyclyl moiety selected from the group consisting of pyrrolidinyl, piperidinyl and morpholinyl; wherein piperidinyl is substituted with two or four substituents selected from methyl.

21. The compound of claim 1 of the formula:

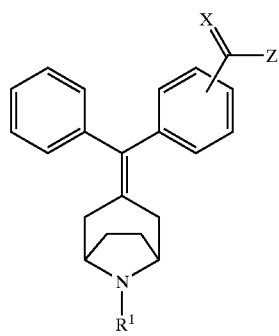

wherein the moiety —C(=X)— is substituted on phenyl at the 3 or 4 position and $R^1$, —C(=X)— and Z are dependently selected from the group consisting of:

| $R^1$ | —C(=X)— | Z |
|---|---|---|
| methyl | -4-C(=O)— | N,N-diethylamino; |
| H | -4-C(=O)— | N,N-diethylamino; |
| allyl | -4-C(=O)— | N,N-diethylamino; |
| 2-(4-fluorophenyl)ethyl | -4-C(=O)— | N,N-diethylamino; |
| 2-(2-thienyl)ethyl | -4-C(=O)— | N,N-diethylamino; |
| 2-(3-indolyl)ethyl | -4-C(=O)— | N,N-diethylamino; |
| 2-cyclohexylethyl | -4-C(=O)— | N,N-diethylamino; |
| 2-phenoxyethyl | -4-C(=O)— | N,N-diethylamino; |
| 2-(4-ethyl-5-oxo-1,4-dihydrotetrazol-1-yl)ethyl | -4-C(=O)— | N,N-diethylamino; |
| 2-phenyl-2-oxoethyl | -4-C(=O)— | N,N-diethylamino; |
| 2-(4-methoxyphenyl)-2-oxoethyl | -4-C(=O)— | N,N-diethylamino; |
| 2-(3-cyanophenyl)-2-oxoethyl | -4-C(=O)— | N,N-diethylamino; |
| 2-(2,3-dihydro-1,4-benzodioxin-6-yl)-2-oxoethyl | -4-C(=O)— | N,N-diethylamino; |
| 2-(3,4-dihydro-2H-1,5-benzodioxepin-7-yl)-2-oxoethyl | -4-C(=O)— | N,N-diethylamino; |
| propyl | -4-C(=O)— | N,N-diethylamino; |
| 2-phenylethyl | -4-C(=O)— | N,N-diethylamino; |
| piperonyl | -4-C(=O)— | N,N-diethylamino; |
| 3-phenylpropyl | -4-C(=O)— | N,N-diethylamino; |
| methyl | -3-C(=O)— | N-methyl-N-(3-fluorophenyl)amino; |
| 2-phenylethyl | -4-C(=S)— | N,N-diethylamino; |
| 2-phenylethyl | -4-C(=O)— | N-ethylamino; |
| 2-phenylethyl | -4-C(=O)— | amino; |
| 2-phenylethyl | -4-C(=O)— | 4-morpholinyl; |
| 2-phenylethyl | -4-C(=O)— | N,N-diisopropylamino; |
| 2-phenylethyl | -4-C(=O)— | N,N-bis(methoxyethyl)amino; |
| 2-phenylethyl | -4-C(=O)— | 1-pyrrolidinyl; |
| 2-phenylethyl | -4-C(=O)— | 2,6-dimethyl-1-piperidinyl; |
| 2-phenylethyl | -4-C(=O)— | N-ethyl-N-(methylallyl)amino; |
| 2-phenylethyl | -4-C(=O)— | N,N-dipropylamino; |
| 2-phenylethyl | -4-C(=O)— | N-t-butylamino; |
| 2-phenylethyl | -4-C(=O)— | N-(2-fluoroethyl)amino; |
| 2-phenylethyl | -4-C(=O)— | N-(2-thiazolyl)amino; |
| 2-phenylethyl | -4-C(=O)— | N-(2-methoxyethyl)amino; |
| 2-phenylethyl | -4-C(=O)— | N-(1H-benzimidazol-2-ylmethyl)amino; |
| 2-phenylethyl | -4-C(=O)— | N-cyclohexylamino; |
| 2-phenylethyl | -4-C(=O)— | N-phenylamino; |
| 2-phenylethyl | -4-C(=O)— | N-[2-(2-imidazolyl)ethyl]amino; |
| 2-phenylethyl | -4-C(=O)— | N-cyclopropylamino; |
| 2-phenylethyl | -4-C(=O)— | N,N-(dimethylaminopropyl)amino; |
| 2-phenylethyl | -4-C(=O)— | N-ethyl-N-(hydroxyethyl)amino; |
| 2-(1,3-benzodioxol-5-yl)ethyl | -4-C(=O)— | N-ethylamino; |
| 2-(1,3-benzodioxol-5-yl)ethyl | -4-C(=O)— | N,N-diethylamino; |
| methyl | -4-C(=O)— | N-ethylamino; |
| H | -4-C(=O)— | N-ethylamino; |
| allyl | -4-C(=O)— | N-ethylamino; |
| 2-(4-methoxyphenyl)ethyl | -4-C(=O)— | N,N-diethylamino; |
| 2-(4-methoxyphenyl)ethyl | -4-C(=O)— | 4-morpholinyl; |
| 2-(4-methoxyphenyl)ethyl | -4-C(=O)— | N-ethylamino; |
| 2-(4-methoxyphenyl)ethyl | -4-C(=O)— | N,N-bis(2-methoxyethyl)amino; |
| 2-(4-methoxyphenyl)ethyl | -4-C(=O)— | 1-pyrrolidinyl; |
| 2-(4-methoxyphenyl)ethyl | -4-C(=O)— | 2,6-dimethyl-1-piperidinyl; |
| 2-(4-methoxyphenyl)ethyl | -4-C(=O)— | N-ethyl-N-(methylallyl)amino; |
| 2-(4-methoxyphenyl)ethyl | -4-C(=O)— | N,N-(di-n-propyl)amino; |
| 2-(4-methoxyphenyl)ethyl | -4-C(=O)— | 2,2,6,6-tetramethyl-1-piperidinyl; |
| 2-(4-methoxyphenyl)ethyl | -4-C(=O)— | N,N-(di-2-propyl)amino; |
| 2-(4-hydroxyphenyl)ethyl | -4-C(=O)— | N-ethylamino; and, |
| 2-(4-hydroxyphenyl)ethyl | -4-C(=O)— | N,N-diethylamino; | or enantiomers, diastereomers or pharmaceutically acceptable salts thereof.

22. The compound of claim 1 of the formula:

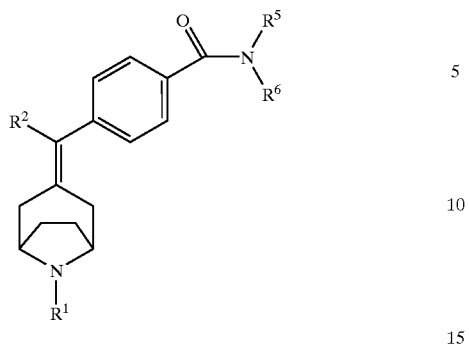

wherein $R^1$, $R^2$, $R^5$ and $R^6$ are dependently selected from the group consisting of:

| $R^1$ | $R^2$ | $(R^5)(R^6)$ |
|---|---|---|
| methyl | 4-MeOPh | (H)(Et); |
| H | 4-HOPh | (H)(Et); |
| methyl | 4-MeOPh | $Et_2$; |
| H | 4-HOPh | $Et_2$; |
| 2-(4-MeOPh)ethyl | 4-MeOPh | $Et_2$; and, |
| 2-(4-HOPh)ethyl | 4-HOPh | $Et_2$; | or enantiomers, diastereomers or pharmaceutically acceptable salts thereof.

23. A pharmaceutical composition comprising a compound of claim 1 and a pharmaceutically acceptable carrier.

24. A method tar the treatment of pain in a subject in need thereof comprising administering to the subject a therapeutically effective amount of compound of Formula (I)

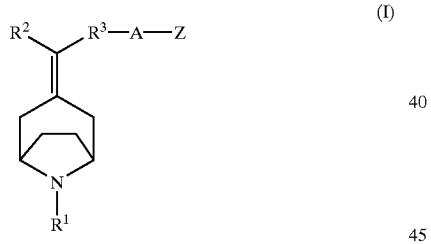
(I)

wherein:

$R^1$ is selected from the group consisting of hydrogen, $C_{1-8}$alkyl, $halo_{1-3}(C_{1-8})$alkyl, $C_{2-8}$alkenyl, $C_{1-8}$alkoxy $(C_{2-8})$alkenyl, $C_{2-8}$alkynyl, $C_{1-8}$alkoxy $(C_{2-8})$ alkynyl, cycloalkyl, cycloalkyl $(C_{1-8})$ alkyl, cycloalkylcarbonyl $(C_{1-8})$ alkyl, cycloalkyl $(C_{2-8})$ alkenyl, cycloalkyl $(C_{2-8})$ alkynyl, heterocyclyl, heterocyclyl $(C_{1-8})$alkyl, heterocyclylcarbonyl $(C_{1-8})$ alkyl, heterocyclyl $(C_{2-8})$ alkenyl, heterocyclyl $(C_{2-8})$alkynyl, aryl, aryl $(C_{1-8})$ alkyl, arylcarbonyl $(C_{1-8})$alkyl, aryl $(C_{2-8})$alkenyl, aryl $(C_{2-8})$alkynyl, arylaminocarbonyl $(C_{1-8})$ alkyl, heteroaryl $(C_{1-8})$ alkyl, heteroarylcarbonyl $(C_{1-8})$ alkyl, heteroaryl $(C_{2-8})$ alkenyl, heteroaryl $(C_{2-8})$ alkynyl, heteroarylaminocarbonyl $(C_{1-8})$ alkyl, $(R^{1a})_2$—N—$(C_{1-8})$ alkyl, $R^{1a}$—O—$(C_{1-8})$ alkyl, $R^{1a}$—S—$(C_{1-8})$ alkyl, $R^{1a}$—SO—$(C_{1-8})$ alkyl and $R^{1a}$—SO$_2$—$(C_{1-8})$ alkyl; wherein heterocyclyl is optionally substituted with one to three substituents independently selected from the group consisting of $C_{1-6}$alkyl, $C_{2-6}$alkenyl, $C_{1-6}$alkoxy, amino, $C_{1-6}$alkylamino, di $(C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, oxo, cyano, trifluoromethyl and trifluoromethoxy; and, wherein aryl and heteroaryl are optionally substituted with one to three substituents independently selected from the group consisting of $C_{1-6}$alkyl, $C_{2-6}$alkenyl, $C_{1-6}$alkoxy, amino, $C_{1-6}$alkylamino, di $(C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy;

$R^{1a}$ is independently selected from the group consisting of hydrogen, $C_{1-8}$alkyl, $C_{1-8}$alkoxy$(C_{1-8})$alkyl, hydroxy $(C_{1-8})$alkyl, $halo_{1-3}(C_{1-8})$alkyl, $halo_{1-3}(C_{1-8})$alkoxy $(C_{1-8})$alkyl, $C_{2-8}$alkenyl, $C_{2-8}$alkynyl, cycloalkyl, cycloalkyl $(C_{1-8})$ alkyl, heterocyclyl, heterocyclyl $(C_{1-8})$ alkyl, heterocyclyl $(C_{1-8})$ alkenyl, heterocyclyl $(C_{1-8})$ alkynyl, aryl, aryl $(C_{1-8})$ alkyl, aryl $(C_{1-8})$ alkenyl, aryl $(C_{1-8})$alkynyl, arylcarbonyl $(C_{1-8})$alkyl, heteroaryl, heteroaryl $(C_{1-8})$ alkyl, heteroaryl $(C_{1-8})$ alkenyl, heteroaryl $(C_{1-8})$ alkynyl and heteroarylcarbonyl $(C_{1-8})$ alkyl; wherein heterocyclyl is optionally substituted with one to three substituents independently selected from the group consisting of $C_{1-6}$alkyl, $C_{2-6}$alkenyl, $C_{1-6}$alkoxy, amino, $C_{1-6}$alkylamino, di $(C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, oxo, cyano, trifluoromethyl and trifluoromethoxy; and, wherein aryl and heteroaryl are optionally substituted with one to three substituents independently selected from the group consisting of $C_{1-6}$alkyl, $C_{2-6}$alkenyl, $C_{1-6}$alkoxy, amino, $C_{1-6}$alkylamino, di $(C_{1-6}$alkyl) amino, $C_{1-6}$alkylcarbonyl, $C_{1-6}$alkylcarbonyloxy, $C_{1-6}$alkylcarbonylamino, $C_{1-6}$alkylthio, $C_{1-6}$alkylsulfonyl, halogen, hydroxy, cyano, trifluoromethyl and trifluoromethoxy;

$R^2$ selected from the group consisting of aryl and heteroaryl optionally substituted with one to three substituents independently selected from the group consisting of $C_{1-6}$alkyl, $C_{2-6}$alkenyl, $C_{1-6}$alkoxy, amino, $C_{1-6}$alkylamino, di $(C_{1-6}$alkyl) amino, $C_{1-6}$alkylcarbonyl, $C_{1-6}$alkylcarbonyloxy, $C_{1-6}$alkyloxycarbonyl, $C_{1-6}$alkylaminocarbonyl, $C_{1-6}$alkylcarbonylamino, $C_{1-6}$alkylthio, $C_{1-6}$alkylsulfonyl, halogen, hydroxy, cyano, trifluoromethyl and trifluoromethoxy; alternatively, when aryl and heteroaryl are substituted with two substituents attached to adjacent carbon atoms, the two substituents can together form a single fused moiety; wherein the moiety is selected from the group consisting of —$(CH_2)_{3-5}$— and —$O(CH_2)_{1-3}O$—;

$R^3$ is selected from the group consisting of aryl and heteroaryl optionally substituted with one or two substituents in addition to the -A-Z moiety independently selected from the group consisting of $C_{1-6}$alkyl, $C_{2-6}$alkenyl, $C_{1-6}$alkoxy, amino, $C_{1-6}$alkylamino, di $(C_{1-6}$alkyl) amino, $C_{1-6}$alkylcarbonyl, $C_{1-6}$alkylcarbonyloxy, $C_{1-6}$alkyloxycarbonyl, $C_{1-6}$alkylaminocarbonyl, $C_{1-6}$alkylcarbonylamino, $C_{1-6}$alkylthio, $C_{1-6}$alkylsulfonyl, halogen, hydroxy, cyano, trifluoromethyl and trifluoromethoxy; alternatively, when aryl and heteroaryl are substituted with two optional substituents attached to adjacent carbon atoms, the two substituents can together form a single fused moiety; wherein the moiety is selected from the group consisting of —$(CH_2)_{3-5}$— and —$O(CH_2)_{1-3}O$—;

A is selected from the group consisting of —C(=X)— and —SO$_2$—;

X is selected from the group consisting of O and S;

Z is selected from the group consisting of —O(R$^4$) and —N(R$^5$)(R$^6$)

R$^4$ is selected from the group consisting of hydrogen, C$_{1-8}$alkyl (optionally substituted with one to three halogen substituents), C$_{1-8}$alkoxy(C$_{1-8}$)alkyl, C$_{2-8}$alkenyl, cycloalkyl, cycloalkyl (C$_{1-8}$)alkyl, heterocyclyl, heterocyclyl (C$_{1-8}$) alkyl, aryl, aryl (C$_{1-8}$) alkyl, heteroaryl, heteroaryl (C$_{1-8}$) alkyl, amino (C$_{1-8}$) alkyl, C$_{1-8}$alkylamino (C$_{1-8}$) alkyl, di (C$_{1-8}$)alkylamino (C$_{1-8}$)alkyl and hydroxy(C$_{1-8}$)alkyl; wherein heterocyclyl is optionally substituted with one to three substituents independently selected from the group consisting of C$_{1-6}$alkyl, C$_{1-6}$alkoxy, C$_{2-6}$alkenyl, cycloalkyl, trifluoromethyl, halogen, hydroxy, oxo and cyano; and, wherein aryl is optionally substituted with one to four substituents independently selected from the group consisting of C$_{1-6}$alkyl, C$_{1-6}$alkoxy, C$_{2-6}$alkenyl, cycloalkyl, —OCH$_2$O—, —O(CH$_2$)$_2$O—, trifluoromethyl, halogen, hydroxy and cyano;

R$^5$ and R$^6$ are independently selected from the group consisting of hydrogen, C$_{1-8}$alkyl (optionally substituted with one to three halogen substituents), C$_{1-8}$alkoxy(C$_{1-8}$)alkyl, C$_{2-8}$alkenyl, cycloalkyl, cycloalkyl (C$_{1-8}$)alkyl, heterocyclyl, heterocyclyl (C$_{1-8}$)alkyl, aryl, aryl (C$_{1-8}$)alkyl, heteroaryl, heteroaryl (C$_{1-8}$) alkyl, amino (C$_{1-8}$) alkyl, C$_{1-8}$alkylamino(C$_{1-8}$) alkyl, di (C$_{1-8}$)alkylamino(C$_{1-8}$)alkyl, aminoimino, aminocarbonyl, aminocarbonyl (C$_{1-8}$) alkyl, aryloxycarbonylamino (C$_{1-8}$) alkyl, heteroaryloxycarbonylamino (C$_{1-8}$) alkyl, hydroxy (C$_{1-8}$) alkyl and trifluoro (C$_{1-4}$)alkoxy; wherein heterocyclyl is optionally substituted with one to three substituents independently selected from the group consisting of C$_{1-6}$alkyl, C$_{1-6}$alkoxy, C$_{2-6}$alkenyl, cycloalkyl, trifluoromethyl, halogen, hydroxy, oxo and cyano; and, wherein aryl is optionally substituted with one to four substituents independently selected from the group consisting of C$_{1-6}$alkyl, C$_{1-6}$alkoxy, C$_{2-6}$alkenyl, cycloalkyl, —OCH$_2$O—, —O(CH$_2$)$_2$O—, trifluoromethyl, halogen, hydroxy and cyano; alternatively, R$^5$ and R$^6$ may, together with the nitrogen to which they are attached, form a fused heterocyclyl moiety optionally substituted with one to four substituents independently selected from the group consisting of C$_{1-6}$alkyl, C$_{1-6}$alkoxy, C$_{2-6}$alkenyl, cycloalkyl, trifluoromethyl, halogen, hydroxy and cyano;

wherein the cycloalkyl in any cycloalkyl containing substituent is a branched or unbranched cyclic aliphatic hydrocarbon chain of three to seven carbon atom members;

wherein the heteroaryl in any heteroaryl containing substituent is an aromatic ring of five or six members wherein the ring has at least one heteroatom member selected from the group consisting of nitrogen, oxygen and sulfur, and wherein said five-membered ring optionally contains up to two additional nitrogens, and wherein said six-membered ring optionally contains from one to three additional nitrogen atoms wherein at most two nitrogen atoms are adjacent;

wherein the heterocyclyl in any heterocyclyl containing substituent is a nonaromatic ring of five to seven members in which one to four members are nitrogen or a nonaromatic ring of five to seven members in which zero, one or two members are nitrogen and one member is oxygen or sulfur, wherein the heterocyclyl optionally contains zero, one or two unsaturated bonds, and wherein optionally up to three carbon members of the hetercyclyl adjacent to nitrogen members is oxo substituted, and wherein optionally, the heterocyclyl ring is fused to a ring selected from the group consisting of a benzene ring, a 5 or 6 membered heteroaryl containing one of O, S or N wherein said heteroaryl optionally contains one additional nitrogen, a 5 to 7 membered alicyclic ring, and a 5 to 7 membered heterocyclyl ring of the same definition as above but absent the option of a further fused ring; and wherein the alkylthio of any alkylthio containing substituent is attached to the rest of the molecule through its sulfur atom;

or enantiomers, diastereomers or pharmaceutically acceptable salts thereof.

25. The method of claim 24 wherein the therapeutically effective amount is from about 0.01 mg/day to about 15,000 mg/day.

* * * * *